(12) United States Patent
Luptak

(10) Patent No.: US 11,933,827 B2
(45) Date of Patent: Mar. 19, 2024

(54) CAPACITIVE SENSING OF HAND PRESENCE AT CONTROL INPUT DEVICE

(71) Applicant: Intuitive Surgical Operations, Inc., Sunnyvale, CA (US)

(72) Inventor: Brian Luptak, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 209 days.

(21) Appl. No.: 17/518,385

(22) Filed: Nov. 3, 2021

(65) Prior Publication Data
US 2022/0137113 A1  May 5, 2022

Related U.S. Application Data

(60) Provisional application No. 63/109,748, filed on Nov. 4, 2020.

(51) Int. Cl.
| | | |
|---|---|---|
| *G01R 27/26* | (2006.01) | |
| *A61B 34/00* | (2016.01) | |
| *A61B 34/35* | (2016.01) | |
| *A61B 34/37* | (2016.01) | |
| *H03K 17/96* | (2006.01) | |

(52) U.S. Cl.
CPC ....... *G01R 27/2605* (2013.01); *H03K 17/962* (2013.01); *A61B 34/35* (2016.02); *A61B 34/37* (2016.02); *A61B 34/70* (2016.02); *H03K 2217/960755* (2013.01)

(58) Field of Classification Search
CPC ............. G01R 27/2605; H03K 17/962; H03K 2217/960755; A61B 34/35; A61B 34/70; A61B 2034/742; A61B 34/74; A61B 34/37; G01V 3/00
See application file for complete search history.

(56) References Cited

U.S. PATENT DOCUMENTS

| | | |
|---|---|---|
| 6,587,750 B2 | 7/2003 | Gerbi et al. |
| 7,598,881 B2 * | 10/2009 | Morgan ............ B60R 21/01534 340/552 |
| 8,073,335 B2 | 12/2011 | Labonville et al. |
| 8,418,073 B2 | 4/2013 | Mohr et al. |
| 8,521,331 B2 | 8/2013 | Itkowitz |

(Continued)

FOREIGN PATENT DOCUMENTS

| | | |
|---|---|---|
| WO | WO-2018112227 A3 | 7/2018 |
| WO | WO-2019099504 A1 | 5/2019 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Amy He
(74) *Attorney, Agent, or Firm* — IP Spring

(57) ABSTRACT

Implementations relate to capacitive sensing of hand presence at a control input device. In some implementations, a control input device includes a support structure, a handle moveable in one or more degrees of freedom with reference to the support structure, and a capacitive sensor circuit electrically coupled to the handle. The handle is isolated from electrical ground and is an antenna for the capacitive sensor circuit.

25 Claims, 10 Drawing Sheets

(56) References Cited

U.S. PATENT DOCUMENTS

| | | | |
|---|---|---|---|
| 8,638,057 B2 | 1/2014 | Goldberg et al. | |
| 2017/0035526 A1* | 2/2017 | Farritor | A61B 1/00128 |
| 2019/0380801 A1 | 12/2019 | Savall et al. | |
| 2019/0380802 A1 | 12/2019 | Savall et al. | |

FOREIGN PATENT DOCUMENTS

| | | |
|---|---|---|
| WO | WO-2019099584 A1 | 5/2019 |
| WO | WO-2019217882 A1 | 11/2019 |
| WO | WO-2021071933 A1 | 4/2021 |

* cited by examiner

CAPACITIVE SENSING OF HAND PRESENCE AT CONTROL INPUT DEVICE

CROSS-REFERENCE TO RELATED APPLICATIONS

The present application claims priority to U.S. Provisional Patent Application No. 63/109,748, filed Nov. 4, 2020 and titled "Capacitive Sensing of Hand Presence at Control Input Device," the entire contents of which are hereby incorporated by reference.

BACKGROUND

Control input devices allow a user to control functions of various types of mechanisms and instruments. For example, teleoperated control systems may allow a user to control functions or movement of a separate device (e.g., a manipulator device) using a control input device. Teleoperated surgical systems, for example, can provide a control input device enabling a user to control various types of medical instruments of a separate patient-side manipulator device to perform surgical procedures for a patient. The medical instruments and connected manipulator arms are controlled to perform the surgical procedures. Actuators of the manipulator device can be controlled by the control input device to cause motion or initiate a function of a medical instrument, camera, or other end effector at the manipulator device that interacts with the patient surgical site. In some examples, the control input device at the operator console can be physically manipulated by the operator in one or more degrees of freedom to control the end effector to be moved in coordination with the control device at the operating site. Other types of teleoperated control systems can provide similar user control over manipulator devices at a work site.

In some types of teleoperated systems, there may be a safety risk stemming from the possibility of the control input device undergoing motion which is unintentional or undetected by the user. In a controlling mode, such unintentional motion may cause corresponding unintended motion of a manipulator device. Some examples include incidental contact to the control input device, or slippage of the control input device from the user's hand due to unexpected impacts or forces. For example, haptic feedback output by motors can push the control input device away from the user's hand if the user's hand does not have a proper grip on the control input device. The teleoperated system may not disconnect the controlling mode of the control input device in such cases of unintended motion.

Some control systems can detect the presence of a user operating the control input devices. This allows control of a manipulator device to be enabled when the user is detected to be operating the control input device, and allows the control to be safely disabled when the user is detected to not be present. In some control systems, the user's presence can be detected using one or more presence sensors. For example, some systems include an operator console at which control input devices are used. An optical detector can detect the presence of an operator's head when the head is positioned to view a video output device of the console. However, such detection does not directly indicate whether the user's hands are ready to use the control input devices.

Some previous presence sensing systems can detect contact of the user's hand with a control input device. For example, some hand sensing systems may rely on optical beam-break or optical line-of-sight sensors to detect hand presence. However, presence detection by these systems may have errors. For example, if the sensors are carefully aligned not to overlap a grippable handle of the control input device, this alignment may cause incidents of false lack of hand detection (false negatives) where the handle occludes the user's hand from detection, or the user's hand avoids detection by the beam in certain hand poses. False detections of a hand (false positives) are also possible for certain types of sensors, e.g., optical sensors that are sensitive to dust and scratches on their surface and to reflectivity of a target object.

SUMMARY

Implementations of the present application relate to capacitive sensing of hand presence at a control input device. In some implementations, a control input device includes a support structure, a handle moveable in one or more degrees of freedom with reference to the support structure, and a capacitive sensor circuit electrically coupled to the handle. The handle is isolated from electrical ground and is an antenna for the capacitive sensor circuit.

Various implementations and examples of the control input device are described. For example, in some implementations, the support structure is coupled to the electrical ground. In some implementations, the control input device further includes an electrical isolation element coupled between the handle and the support structure. In some examples, the electrical isolation element includes a bearing. For example, the bearing can include a first bearing portion coupled to the support structure and a second bearing portion coupled to the handle. In various implementations, the first bearing portion includes a first electrically insulative layer that contacts the support structure, and/or the second bearing portion includes a second electrically insulative layer that contacts the handle. In further examples, the electrical isolation element includes a drive mechanism configured to transmit force from an actuator to the handle. For example, the drive mechanism can include a gear mechanism including multiple interlocking gears coupling the handle to the support structure, and at least one of the multiple interlocking gears includes an insulator that electrically isolates the handle from the electrical ground via the gear mechanism.

In some implementations, the capacitive sensor circuit is configured to detect a capacitance of the handle with reference to the electrical ground based on an electrical signal applied from the capacitive sensor circuit to the handle. For example, the capacitive sensor circuit can output (or cause output of) an oscillation (e.g., electrical oscillation signal) on the handle and can sense the oscillation to determine a capacitance of the handle with reference to the electrical ground. In some implementations, the handle is rotatable in one or more rotational degrees of freedom about corresponding one or more rotational axes of the handle with reference to the support structure. For example, the handle can include a grip member that is rotatably coupled to a central portion of the handle. In some examples, the grip member is coupled to the central portion by a coupling that includes an insulator providing electrical isolation of the handle from the electrical ground, and the insulator can include an anodized surface on the coupling. In further examples, the control input device includes a finger loop coupled to the grip member, and the finger loop includes conductive metallic elements and is electrically conductive. In some implementations, the handle includes a grip member, the control input device further includes an element coupled to the grip member, and the element is configured to cause the grip member to move by translating along a linear axis of the handle with reference to the support structure.

In some implementations, the control input device further includes a cylindrical member rotatable about a central axis of the handle and providing a roll degree of freedom to the handle, and a rotary electrical connector, e.g., a slip ring, coupled between the capacitive sensor circuit and the cylindrical member. In various implementations, the control input device is mechanically grounded or is mechanically ungrounded. In some implementations, the control input device further includes one or more control input sensors that sense one or more positions, one or more orientations, or one or more positions and orientations of the handle in the one or more degrees of freedom. In some implementations, the control input device is included in a teleoperated system, the teleoperated system includes a controlling mode in which movement of the handle in the one or more degrees of freedom activates one or more functions of a manipulator device of the teleoperated system, and a capacitance sensed by the capacitive sensor circuit indicates presence of a hand of a user at the control input device and enables activation of the controlling mode of the teleoperated system. In some implementations, the control input device is included in a teleoperated surgical system, and the support structure is coupled to a gimbal mechanism providing multiple degrees of freedom to the support structure and to the handle.

In some implementations, a control input device includes a support structure, a handle moveable in one or more degrees of freedom, a bearing coupled between the handle and the support structure, and a capacitive sensor. The bearing includes an insulator, and the handle is an antenna for the capacitive sensor and is isolated from the electrical ground through the bearing by the insulator. In some implementations, the support structure is coupled to the electrical ground.

Various implementations and examples of this control input device are described. For example, in some implementations, the bearing includes a first element and a second element, the first element coupled to the support structure and including an electrically insulating layer contacting the support structure, and the second element coupled to the handle. In some implementations, the bearing includes a first element coupled to the support structure, a second element coupled to the handle, and a plurality of balls positioned between the first element and the second element, the balls being made of an electrically insulative material. In some implementations, the handle comprises a proximal end and a distal end, and a roll axis is defined through the proximal and distal ends, wherein the bearing supports a roll degree of freedom of the handle about the roll axis with reference to the support structure. In some implementations, the control input device further includes a cylindrical member rotatable about a roll axis of the handle and which provides a roll degree of freedom to the handle, wherein the cylindrical member is coupled to the bearing. In some implementations, the control input device further includes a gear mechanism that includes a first gear coupled to a second gear, wherein the first gear is coupled to the handle and the second gear is coupled to the support structure, and at least one of the gears include an insulator that electrically isolates the handle from the electrical ground via the gear mechanism.

In some implementations, a control input device includes a support structure, a handle moveable in one or more degrees of freedom, a drive mechanism coupled between the handle and the support structure, and a capacitive sensor. The drive mechanism includes an insulator, and the handle is an antenna for the capacitive sensor and is isolated from an electrical ground through the drive mechanism by the insulator.

Various implementations and examples of this control input device are described. For example, in some implementations, the support structure is coupled to the electrical ground. In some implementations, the drive mechanism includes a gear mechanism including a first gear engaging a second gear, wherein the first gear is coupled to the handle and the second gear is coupled to the support structure, and at least one of these gears includes the insulator. In various implementations, the insulator includes an insulative layer on gear teeth of the first and/or second gear, the insulator includes an anodized surface on gear teeth of the first and/or second gear, and/or the insulator is an insulative portion of the first and/or second gear that is coupled to an electrically conductive portion of the first and/or second gear. In some implementations, the control input device further includes a rotatable cylindrical member coupling the gear mechanism to the handle, the cylindrical member extending through an aperture of the first gear, wherein the insulator includes an insulating layer or sleeve provided on at least a portion of the cylindrical member, and/or the insulator is an insulating layer on a surface of the first gear within the aperture. In some implementations, the control input device further includes a bearing coupled between the handle and the support structure, the bearing including a second insulator that electrically isolates the handle from the electrical ground via the bearing.

In some implementations, a control input device includes a support structure moveable in one or more degrees of freedom, a control input sensor that senses a position and/or orientation of the support structure in the one or more degrees of freedom, and a capacitive sensor coupled to the support structure. The capacitive sensor includes an antenna, and the antenna includes a handle coupled to the support structure and isolated from an electrical ground. Various implementations and examples of this control input device are described. For example, in some implementations, the support structure is coupled to the electrical ground. In some implementations, the handle is isolated from the electrical ground based on a bearing including an insulator and/or a drive mechanism including an insulator.

In some implementations, a method includes sending an electrical signal from a capacitive sensor circuit to a handle of a control input device, wherein the handle is isolated from an electrical ground via an isolating element. The method senses, by the capacitive sensor circuit, a capacitance of the handle based on the electrical signal, and determines that a user presence has been sensed at the control input device in response to the sensed capacitance of the handle satisfying one or more detection criteria, e.g., a threshold.

In some implementations of the method, the handle is an antenna for the capacitive sensor circuit, the user presence includes user contact received at a grip portion of the handle, and the isolating element includes a bearing including an insulator and/or a drive mechanism including an insulator. In some implementations, the method further includes sensing, by the capacitive sensor circuit, a second capacitance of the handle based on the electrical signal, and determining that the user presence has been removed from the control input device in response to the capacitance of the handle not satisfying the one or more detection criteria. In some implementations, the handle is moved by a hand of a user in one or more degrees of freedom, the control input device is included in a teleoperated system, and in response to determining that user presence has been sensed, a controlling mode of the teleoperated system is activated in which movement of the handle in the one or more degrees of freedom activates one or more functions of a manipulator device of the teleoperated system. In some implementations, the capacitive sensor circuit is coupled to the handle by an electrical resistance element, and sensing the capacitance includes sensing a phase lag of the electrical signal, the phase lag being proportional to an RC time constant of the resistance element and the handle. In some implementations, sending the electrical signal is performed by an LC oscillator, and sensing the capacitance includes sensing a change in frequency of the electrical signal that is proportional to the capacitance.

In some implementations, a control input device includes means for sending an electrical signal to a handle of a control input device, wherein the handle is isolated from an electrical ground via an isolating element. The control input device includes means for sensing a capacitance of the handle based on the electrical signal and means for determining that a user presence has been sensed at the control input device in response to the sensed capacitance of the handle satisfying one or more detection criteria.

DETAILED DESCRIPTION

Figure 1:
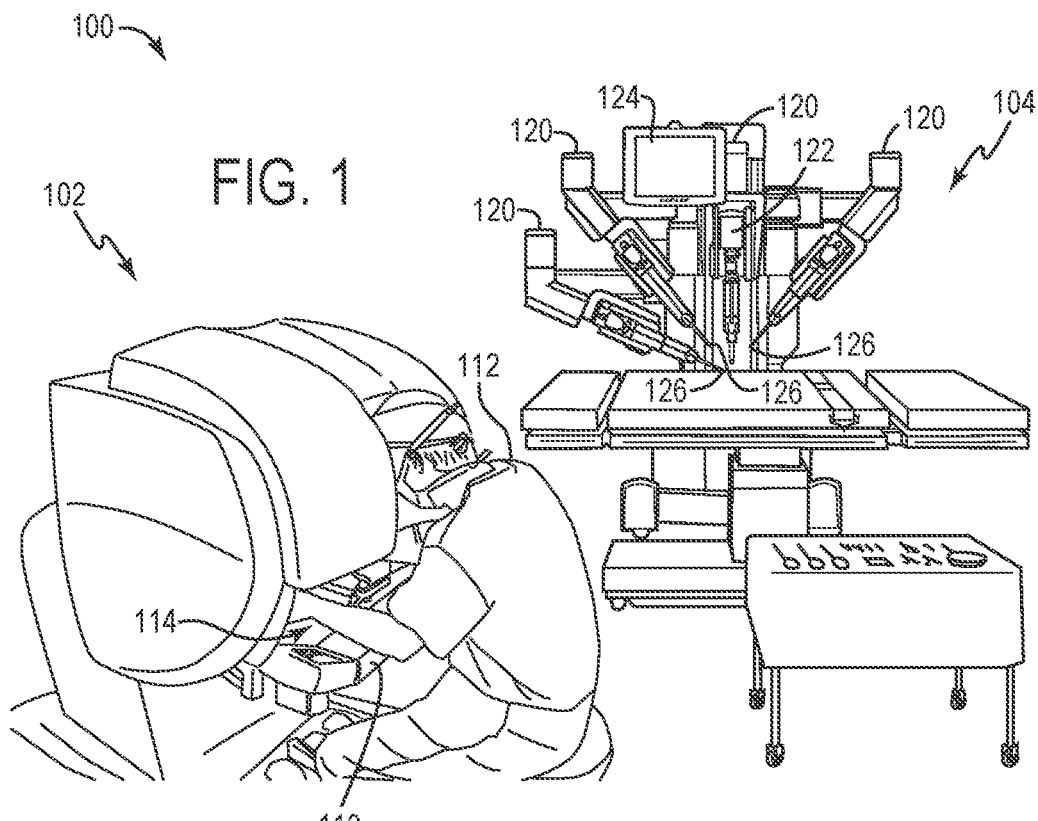
FIG. 1 is a diagrammatic illustration of an example implementation of a teleoperated system which can be used with one or more features disclosed herein, according to some implementations.

One or more implementations described herein relate to a capacitive sensing system that detects hand presence at a control input device. The hand presence sensing system senses the presence of a hand contacting a control input device or positioned near to the device. In some implementations, the control input device includes a support structure coupled to electrical ground, a handle coupled to the support structure, and a capacitive sensor circuit electrically coupled to the handle. The handle is isolated from the electrical ground and is an antenna for a capacitive sensor that includes the sensor circuit. In some examples, one or more grip members and an outer housing portion of the handle can be the antenna for the capacitive sensor.

In various implementations, one or more electrical isolation elements are coupled between the handle and the support structure to isolate the handle from the electrical ground and allow effective capacitive sensing using the handle. For example, an electrical isolation element can be a rotary bearing, such as a ball bearing, that includes a first bearing portion coupled to (e.g., contacting) the support structure and a second bearing portion coupled to (e.g., contacting) the handle. At least one of these bearing portions includes an electrically insulative layer that is coupled to the support structure or handle, such as an anodized surface or an insulative layer made of insulative material (e.g., aluminum oxide). In another example, an electrical isolation element can be a drive mechanism including, e.g., a gear mechanism with multiple interlocking gears coupling the handle to the support structure. At least one gear includes an insulator that electrically isolates the handle from the electrical ground via the gear mechanism.

In some implementations, the capacitive sensor can detect a capacitance of the handle based on sensing an electrical signal (e.g., an oscillation signal) sent from the capacitive sensor to the handle. A rotary electrical connector (e.g., slip ring) can be coupled between the capacitive sensor and a cylindrical member that is coupled to the handle, allowing signals to be transmitted and sensed on a handle that is permitted continuous rotation about an axis. In some examples, the control input device can be included in a teleoperated system, and in response to detecting a capacitance that satisfies one or more detection criteria (e.g., a threshold), a controlling mode of the teleoperated system is activated in which movement of the handle activates one or more functions of a manipulator device, such as corresponding movement of the manipulator device.

Features described herein provide a presence sensing system of a control input device with several advantages. The capacitive sensing system allows detection of contact of a hand of a user with the control input device. Controlling mode of a teleoperated system can be enabled if the user's hand is detected to be in contact with the control input device, thus avoiding or otherwise reducing unintended motion of a controlled manipulator device. This allows a teleoperated system to enter a controlling mode more safely than in systems providing no such hand presence detection.

Furthermore, features described herein provide robust detection of a user's hand on or near the control input device. Features include capacitively sensing the user's hand at the handle of the control input device, which removes or otherwise reduces the possibility of false-negatives and false-positives that may be present in an optical-based sensing system by precisely sensing the user's contact with the control input device regardless of hand position. A handle of a control input device is used as an antenna in a capacitive sensing system, where the handle is isolated from electrical ground to provide high sensitivity for capacitive sensing. This isolation is obtained by controlling electrical (conductive and insulating) properties of components in the control input device. For example, bearings and drivetrain are insulated and a sense signal is connected to a rotating handle via a rotary connector. Features of the presence sensing system can therefore reliably determine whether the user's hand is in contact with the control input device, which is valuable information in determining the user's intent and can help mitigate the safety risks when activating a controlling mode in a teleoperated system or other type of control system. Using various described features, determination by a system to enter and exit controlling mode, or change other states of a control system, is made more easily, reliably, and robustly. Various implementations described herein are compact and inexpensive.

The terms "center," "parallel," "perpendicular," "aligned," or particular measurements in degrees, Hertz, or other units as used herein need not be exact and can include typical engineering tolerances. Some implementations herein may relate to various objects in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded unit or device is constrained with respect to possible position and orientation motion in a large working environment (e.g., an operating area or room). Also, such a unit is kinematically coupled to the ground (e.g., mechanically supported by a console, supports, or other object attached to the ground). As used herein, the term "proximal" refers to an element that is close to (or closer to) a mechanical ground and the term "distal" refers to an element that is away from (or further from) a mechanical ground. The term "finger," as used herein, refers to any digit of the hand, e.g., thumb, index finger, middle finger, ring finger, or pinky finger.

FIG. 1 is a diagrammatic illustration of an example teleoperated surgical system 100 which can be used with one or more features disclosed herein. Other types of control systems, teleoperated systems, or master-slave systems can be used in various implementations including one or more described features. Teleoperated surgical system 100 includes a user control system (e.g., surgeon's console) 102 and a manipulator system 104.

In this example, the user control system 102 includes a viewer 213 (shown in FIG. 2) where an image of a worksite is displayed during an operating procedure using the system 100. For example, the image can be displayed by a display device, such as one or more display screens, to depict a surgical site during a surgical procedure. A support 110 is provided on which a user 112, e.g., an operator such as a surgeon, can rest forearms while gripping control input devices, such as control input devices 210 and 212 shown in FIG. 2. The control input devices 210 and 212 are positioned in a workspace 114 disposed inwardly beyond the support 110. When using the user control system 102, the user 112 can sit in a chair in front of the control system 102, position the user's head/eyes in front of the viewer 213, and grip the control input devices 210 and 212, one in each hand, while resting forearms on the support 110.

A manipulator system 104 is also included in the teleoperated system 100. For example, manipulator system 104 can be a slave device in this example, or can alternatively be a different type of slave device or other controlled device. In some implementations as shown, during a surgical procedure, the manipulator system 104 can be positioned close to a surgical site located with reference to a patient or model disposed on an operating table or other type of worksite). In various implementations, manipulator system 104 can remain stationary until a particular procedure or stage of a procedure is completed, or can move relative to a work site.

Manipulator system 104 can include one or more manipulator devices that can include manipulator arm assemblies 120. In some examples, an arm assembly 120 can include multiple links rotatably coupled to each other. Portions of the arm assembly 120 can be actuated with a motor and sensed about rotational axes. In some examples, one or more of the arm assemblies 120 can be configured to hold a manipulator device such as an image capturing device, e.g., an endoscope 122, which can provide captured images of a portion of the surgical site. In some implementations, the captured images can be transmitted to the viewer 213 of the user control system 102 and/or transmitted to one or more other displays, e.g., a display 124 coupled to the manipulator system 104.

In some examples, each of the other arm assemblies 120 may include a manipulator device such as a surgical tool 126. Each surgical tool 126 can include a surgical end effector, e.g., for treating tissue of the patient. An end effector can be provided the degrees of freedom provided by, e.g., the rotation of link members of the associated arm assembly, linear motion by an end effector mechanism, etc. Components in the arm assembly 120 can function as force transmission mechanisms to receive teleoperated servo actuation forces and redirect the received forces to operate components of the end effector. An end effector can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. End effector mechanisms can include flexible elements, articulated "snake" arms, steerable guide tubes, catheters, scalpel or cutting blade, electro-surgical elements (e.g., monopolar or bipolar electrical instruments), harmonic cutter, scissors, forceps, retractors, dilators, clamps, cauterizing tools, needles, needle drivers, staplers, drills, probes, scopes, light sources, guides, measurement devices, vessel sealers, laparoscopic tools, or other tip, mechanism or device. One example of a surgical manipulator arm is a da Vinci® surgical system instrument manipulator arm in surgical systems commercialized by Intuitive Surgical, Inc. of Sunnyvale, California.

In this example, the arm assemblies 120 can be caused to move and articulate the surgical tools 126 in response to manipulation of corresponding control input devices, e.g., control input devices 210 and 212 (shown in FIG. 2) at the user control system 102 by the user 112. This arrangement allows user 112 to, for example, direct surgical procedures at internal surgical sites through minimally invasive surgical apertures. For example, one or more actuators coupled to the arm assemblies 120 can output forces to cause links or other portions of the arm assemblies to move in particular degrees of freedom in response to control signals received from the user control system 102. For example, movement of an arm and end effector in one or more degrees of freedom can correspond to movement in one or more degrees of freedom of an associated control input device handle by a user. The user control system 102 can be used within a physical environment (e.g., an operating room) with the manipulator system 104 or can be positioned more remotely from the manipulator system 102, e.g., at a different location than the manipulator system.

Some implementations of the teleoperated system 100 can provide different modes of operation. In some examples, in a non-controlling mode (e.g., safe mode) of the teleoperated system 100, the controlled motion of the manipulator system 104 is disconnected from the control input devices of the user control system 102, such that movement and other manipulation of the control input devices does not cause motion of the manipulator system 104. In a controlling mode of teleoperated system 100 (e.g., following mode, in which one or more slave manipulators follow a corresponding control input device), motion of the manipulator system 104 can be controlled by the control input devices 210 and 212 of the user control system 102 such that movement and other manipulation of control input devices 210 and 212 causes motion of the manipulator system 104, e.g., during a surgical procedure. For example, the controlled functions of the manipulator device can include movement of the manipulator device. In some examples, the control input devices are provided with the same degrees of freedom as manipulator devices of the manipulator system 104 to provide the user with telepresence, e.g., the perception that the control input devices are integral with the instruments so that user 112 has a strong sense of directly moving instruments as if present at the work site.

Some implementations can be or include a teleoperated medical system such as a da Vinci® surgical system (e.g., a Model IS3000 or IS4000, marketed as the da Vinci Si® or da Vinci Xi® surgical system), commercialized by Intuitive Surgical, Inc. of Sunnyvale, California. However, features disclosed herein may be implemented in various ways, including in implementations at least partially computer-controlled, controlled via electronic control signals, manually controlled via direct physical manipulation, etc. Implementations on da Vinci® surgical systems are merely exemplary and are not to be considered as limiting the scope of the features disclosed herein. For example, different types of teleoperated systems having slave devices at worksites can make use of actuated controlled features described herein. Other, non-teleoperated systems can also use one or more described features, e.g., various types of control systems and devices, peripherals, etc.

For example, in various implementations, other types of computer-assisted teleoperated systems can be used with one or more features described herein, in addition to surgical systems. Such teleoperated systems can include controlled manipulator or slave devices of various forms. For example, submersibles, hazardous material disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include slave devices for sensory transmission (conveyed visual, auditory, etc. experience), manipulation of work pieces or other physical tasks, etc., and may use mechanically grounded and/or ungrounded control input devices to remotely control the slave devices. Any such teleoperated systems can be used with the various features described herein.

In some implementations, a controlled manipulator device can be a virtual representation of device, e.g., presented in a graphical simulation provided by a computing device coupled to the teleoperated system 100. For example, a user can manipulate the control input devices 210 and 212 of the user control system 102 to control a displayed representation of an end effector in virtual space of the simulation, similarly as if the end effector were a physical object coupled to a physical manipulator device.

Figure 2:
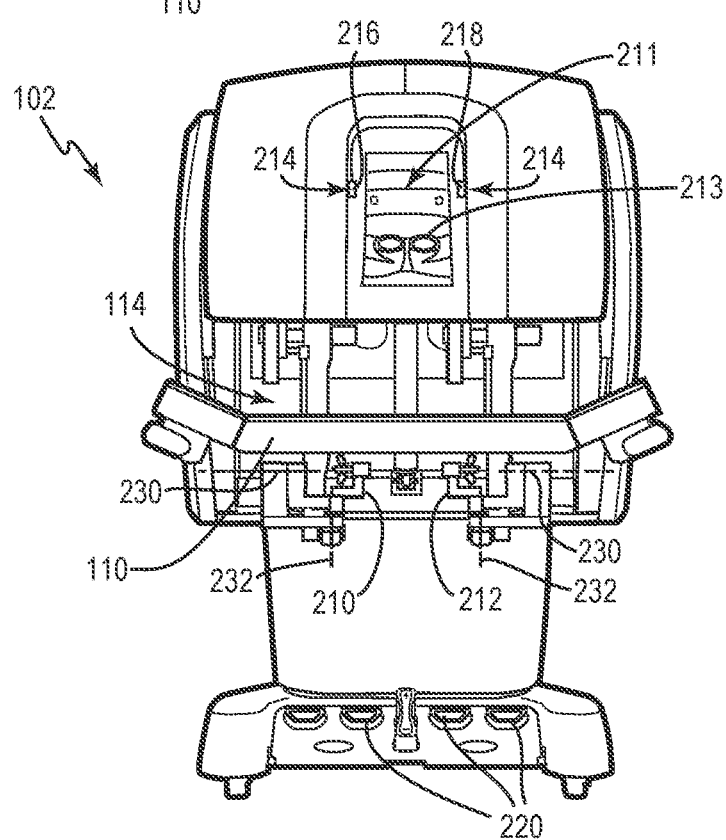
FIG. 2 is a front elevational view of an example user control system as shown in FIG. 1, according to some implementations.

FIG. 2 is a front elevational view of an example user control system 102 as described above for FIG. 1. User control system 102 includes a viewer 213 that provides a display of images of a worksite during a procedure using the teleoperated system 100. The viewer 213 can be positioned within a viewing recess 211 in which the user 112 can position his or her head to view images displayed by the viewer 213. When using the user control system 102, the user 112 can sit in a chair (or stand) in front of user control system 102 and position his or her head within the recess 211 such that his or her eyes are positioned in front of the viewer 213.

In some implementations, one or more user presence sensors 214 can be positioned at one or more locations of the user control system 102 to detect the presence of a user's head located next to or near to the user control system 102. In this example, the user presence sensors 214 can sense a presence of a user's head within recess 211. For example, an electromagnetic sensor (e.g., optical sensor) can be used for a presence sensor. In some examples, the optical sensor can include an emitter 216 and a detector 218. A beam of infrared or other wavelength of light is emitted from one side of recess 211 by emitter 216, and the beam is detected on the other side of the recess by detector 218. If the beam is interrupted from detection by the detector, e.g., due to the user's head blocking the beam, then the system determines that a user's head is within the recess and that the user is in a proper position to use the control input devices of the user control system 102.

Additional presence sensors of user control system 102 include capacitive sensors provided on control input devices 210 and 212, as described in various implementations herein.

Two control input devices 210 and 212 are provided for user manipulation. In some implementations, each control input device 210 and 212 can be configured to control motion and functions of an associated arm assembly 120 of the manipulator system 104. For example, a control input device 210 or 212 can be moved in a plurality of degrees of freedom to move a corresponding end effector of the manipulator system 104 in corresponding degrees of freedom. In some implementations, control input devices 210 and 212 are manual input devices which can be moved in all six Cartesian degrees of freedom. The control input devices 210 and 212 are positioned in workspace 114 inwardly beyond the support 110. For example, a user 112 can rest forearms while gripping two control input devices 210 and 212, with one control input device in each hand. The user also positions his or her head within the viewing recess 211 to view the viewer 213 as described above while manipulating the control input devices 210 and 212. Various examples of portions of input devices that can be used as control input devices 210 and 212 are described below.

Some implementations of user control system 102 can include one or more foot controls 220 positioned below control input devices 210 and 212. The foot controls 220 can be depressed, slid, and/or otherwise manipulated by a user's feet to input various commands to the teleoperated system while the user is sitting at the user control system 102.

Figure 3:
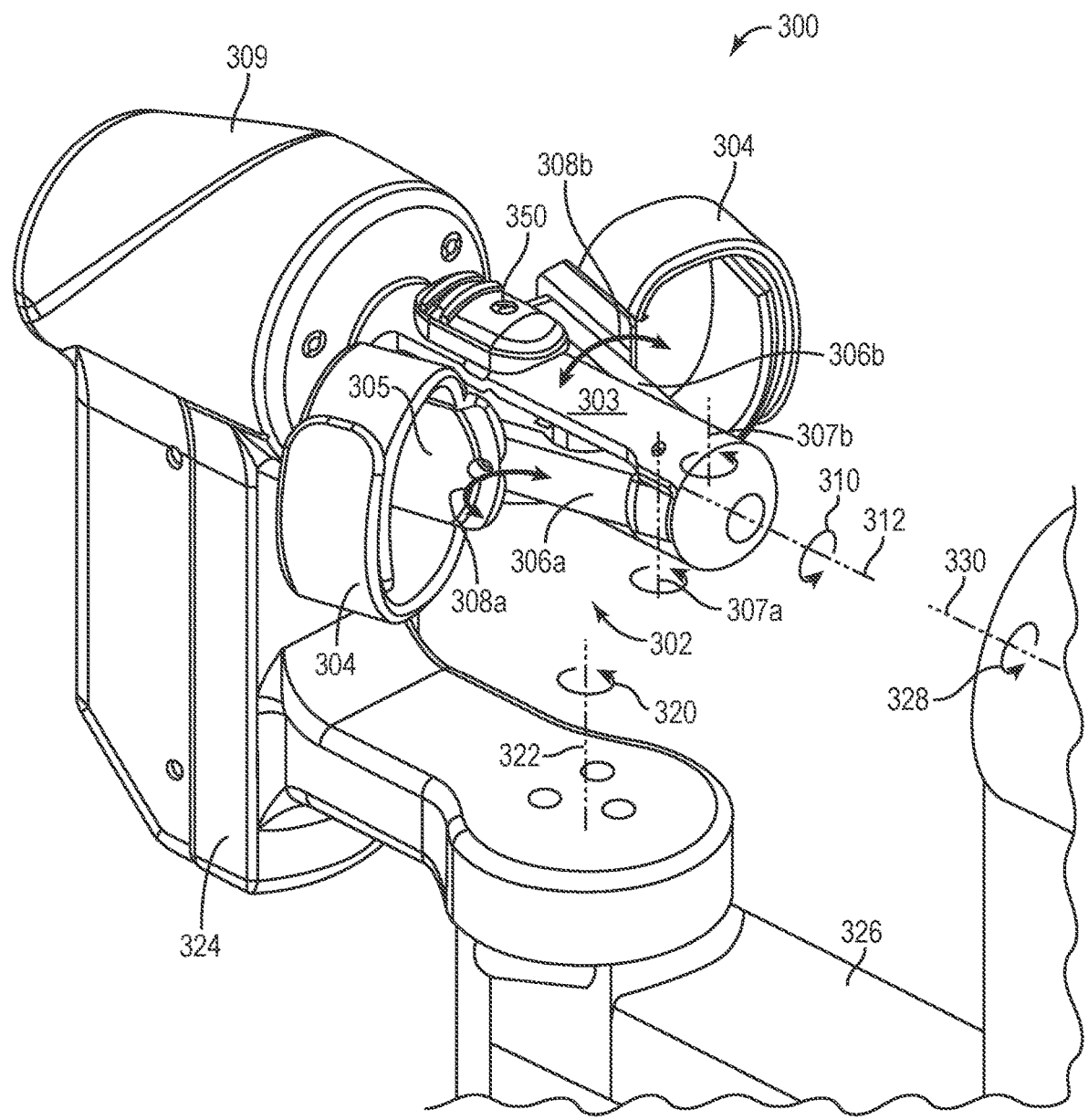
FIG. 3 is a perspective view of an example portion of a control input device which can include one or more features described herein, according to some implementations.

FIG. 3 is a perspective view of an example device portion 300 of a control input device which can include one or more features described herein, according to some implementations. In some implementations, the control input device can be part of a system in which user input provided via the control input device is used to control one or more device functions. For example, the system can be a teleoperated system in which the control input device controls a manipulator device. For example, device portion 300 can be used as a portion of a control input device such as control input device 210 or 212 as described above with reference to FIGS. 1 and 2, or portion 300 can be included in a different control device. In some implementations, the device portion 300 includes one or more gimbal mechanisms.

Device portion 300 includes a handle 302 which is contacted by a user to manipulate the control input device. In this example, the handle 302 includes two grips that each include a finger loop 304 and a grip member 306 (grip members 306a and 306b). The two grip members 306 are positioned on opposite sides of a central portion 303 of the handle 302, and the grip members 306 can be grasped, held, or otherwise contacted by a user's fingers. Each finger loop 304 is attached to a respective grip member 306 and can be used to secure a user's fingers to the associated grip member 306. In this example, finger contacts 305 can be connected or formed at the unconnected end of the grip members 306a and 306b to provide surfaces to contact the user's fingers. The user may also contact other portions of handle 302 while grasping the grip members 306.

Each grip member 306 and finger loop 304 can be moved in an associated degree of freedom 308 (e.g., 308a and 308b). In some examples, the grip members 306a and 306b are each coupled to the central portion 303 of the handle 302 at respective rotational couplings, allowing rotational movement of the grip members about grip axes 307a and 307b, respectively, with respect to the central portion 303. Each grip member 306a and 306b can be moved in an associated degree of freedom 308a about axis 307a and degree of freedom 308b about axis 307b, respectively, e.g., by a user contacting the grip members. For example, in some implementations the grip members 306a and 306b can be moved simultaneously in a pincher-type of movement (e.g., toward or away from each other). In various implementations, a single grip member 306 and finger loop 304 can be provided, or only one of the grip members 306 can be moved in the degree of freedom 308 while the other grip member 306 can be fixed with reference to the handle 302. For example, the positions of grip members 306a and 306b in their degrees of freedom can control corresponding rotational positions of an end effector or component thereof.

One or more grip sensors (not shown) can be coupled to the handle 302 and/or other components of the device portion 300 and can detect the positions of the grip members 306a and 306b in their degrees of freedom 308. The grip sensors can send signals describing sensed positions and/or motions to a control unit of the teleoperated system 100. In some modes or implementations, the control unit can provide control signals to a manipulator device, e.g., manipulator system 104. For example, the positions of the grip members 306a and 306b in degrees of freedom 308a and 308b can be used to control any of various degrees of freedom of an end effector of the manipulator system 104.

Various implementations of the device portion 300 can provide one or more active actuators (e.g., motors, voice coils, etc.) to output active forces on the grip members 306 in the degrees of freedom 308. For example, a sensor and/or actuator can be housed in central portion 303 or in housing 309 and coupled to the grip members 306 by a transmission. Some implementations can provide one or more passive actuators (e.g., brakes) or springs between the grip members 306 and the central portion 303 of the handle 302 to provide motion resistance in particular directions of the grips (e.g., movement in directions toward each other in degree of freedom 308).

Handle 302 is additionally provided with a rotational degree of freedom 310 about a roll axis 312 defined between a first end and second end of the handle 302. The roll axis 312 is a longitudinal axis in this example that extends approximately along the center of central portion 303 of handle 302. Handle 302 can be rotated about axis 312 with respect to a support member of the device portion 300, such as a support member that includes housing 309. For example, a user can rotate the grip members 306 and central portion 303 as a single unit around the axis 312, with respect to housing 309, to provide control of a manipulator device, such as an end effector of the manipulator system 104 or other element of manipulator system 104.

One or more control input sensors (not shown) can be coupled to handle 302 to detect the orientation of handle 302 in rotational degree of freedom 310. For example, the sensor can send signals describing the orientation to a control unit of teleoperated system 100 which can provide control signals to manipulator system 104 similarly as described above. For example, rotation of handle 302 in degree of freedom 310 can control a particular degree of freedom of an end effector of manipulator system 104 that is different than a manipulator degree of freedom controlled by degree of freedom 308 of grip members 306.

Some implementations of device portion 300 can provide one or more actuators to output forces on handle 302 (including grip members 306 and finger loops 304) in the rotational degree of freedom 310. For example, a sensor and/or actuator can be housed in housing 309 and coupled to handle 302 by a shaft extending through central portion 303 of handle 302.

In various implementations, handle 302 can be provided with additional degrees of freedom. For example, a rotational degree of freedom 320 about a yaw axis 322 can be provided to handle 302 at a rotational coupling between an elbow shaped link 324 and a link 326, where the elbow shaped link 324 is coupled to handle 302 (e.g., at housing 309). In this example, yaw axis 322 intersects and is orthogonal to the roll axis 312. For example, yaw axis 322 can be similar to axis 232 shown in FIG. 2. Additional degrees of freedom can similarly be provided. For example, link 326 can be elbow-shaped and a rotational coupling can be provided between the other end of link 326 and another link (not shown). A rotational degree of freedom 328 about an axis 330 can be provided to the handle 302 at the rotational coupling. For example, axis 330 can be similar to axis 230 shown in FIG. 2. In some examples, the device portion 300 can allow movement of handle 302 within the workspace 114 of the user control system 102 with a plurality of degrees of freedom, e.g., six degrees of freedom including three rotational degrees of freedom and three translational degrees of freedom. One or more additional degrees of freedom can be sensed by control input sensors and/or actuated by actuators (motors, etc.) similarly as described above for degrees of freedom 308 and 310. In some implementations, each additional degree of freedom of handle 302 can control a different degree of freedom (or other motion) of an end effector of manipulator system 104.

In an example implementation, handle 302 is mechanically grounded, e.g., supported in space by a kinematic chain with an end stationary at mechanical ground, such as a floor, wall, or ceiling. For example, housing 309 can be coupled to a mechanical linkage that is coupled to the ground or an object connected to the ground, providing a stable platform for the use of device portion 300. For example, a grounded mechanical linkage can be connected to the support member, e.g., with one or more rotary couplings, ball joints, or other couplings, including linear joints. The mechanical linkage can provide six or more degrees of freedom to handle 302. In some implementations, one or more links in the linkage can include links 324 and 326.

In some examples, the support member can be coupled to a serial kinematic chain, the proximal end of which is mechanically grounded. The kinematic chain can include multiple members or links that are rotatably coupled to one or more other members or links of the chain, e.g., by rotational or linear couplings. The rotational axes of the chain can be sensed and/or driven by sensors and/or actuators. Some implementations can provide additional actuated and/or sensed motion of the kinematic chain, e.g., about axes extending lengthwise through one or more members. In some implementations, multiple members of the kinematic chain form a gimbal mechanism that allows handle 302 to be rotated about the rotational axes of the chain. In some implementations, handle 302 can also be translated in at least three linear degrees of freedom allowed by the kinematic chain.

Various kinematic chains, linkages, gimbal mechanisms, flexible structures, or combinations of two or more of these can be used with the mechanically grounded hand controller in various implementations to provide one or more degrees of freedom to the hand controller. Some examples of such implementations are described in U.S. Pat. No. 6,714,839 B2, incorporated herein by reference.

In the described example, handle 302 includes one or more control switches 350, e.g., coupled to the central portion 303 or to mechanisms within central portion 303. For example, two control switches 350 can be positioned on opposite sides of axis 312, and/or additional control switches can be provided. In some examples, a control switch 350 has a portion that can slide parallel to the axis 312, e.g., as directed by a user's finger, or the control switch portion can be depressed. In some implementations, control switch 350 can be a ring or collar that fully or partially surrounds central portion 303 and can be slid up or down central portion 303 to multiple positions. In some implementations, control switch 350 can be moved to various positions to provide particular command signals, e.g., to select functions, options, or modes of the control console and/or control input device (e.g., a controlling mode or non-controlling mode as described herein), to command a manipulator device or other system in communication with the control input device, etc.

Handle 302 also includes a presence sensing system including one or more capacitive sensors that can detect the presence of a user's hand operating the handle. Various implementations of presence sensors are described below.

One or more features described herein can be used with other types of control input devices. For example, device portion 300 can be or be a portion of a mechanically ungrounded control input device which is free to move in space and is disconnected from ground. As used herein, a mechanically ungrounded control input device refers to a control input device that is unconstrained with respect to possible position, orientation, and motion in a working environment (e.g., an operating area or room). Also, such a control device is kinematically separated from the ground, e.g., not mechanically supported by a console, supports, or other object contacting the ground. Location and motion of an ungrounded control input device can be sensed in its workspace using sensors included in the control input device and/or sensors positioned external to the control input device. In some implementations, a mechanically ungrounded control device may be in tethered or untethered connection with one or more associated components such as control processors, data sources, sensors, power supplies, etc. For example, the control device may be tethered, e.g., connected physically to these components via a cable or wire, or untethered, e.g., not physically connected to such components and in communication with the components via wireless communication signals.

In some examples of mechanically ungrounded control input devices, one or more handles similar to handle 302 and/or grip members 306 can be coupled to a mechanism worn on a user's hand and which is ungrounded, allowing the user to move grips freely in space. In some examples, the positions of the grips relative to each other and/or to other portions of the handle can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Mechanically ungrounded control input devices can use capacitive presence sensing features as described herein to detect whether a user is holding the control input device. Some examples of ungrounded control input devices are described in U.S. Pat. No. 8,543,240 B2 (filed Sep. 21, 2010) and U.S. Pat. No. 8,521,331 B2 (filed Nov. 13, 2008), both incorporated herein by reference in their entireties.

Figure 4:
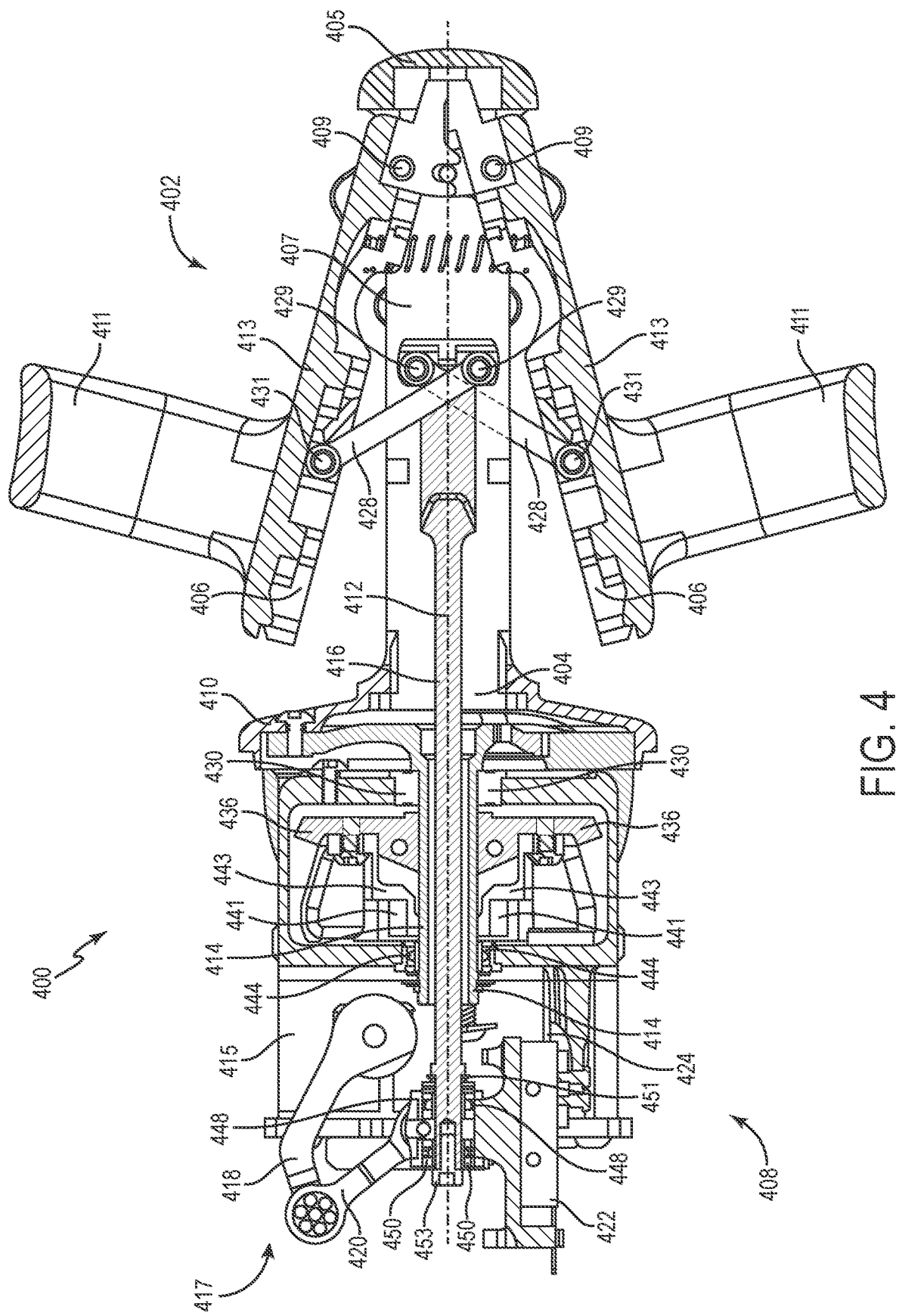
FIGS. 4-6 are top, side, and perspective sectional views, respectively, of an example portion of a control input device including one or more features described herein, according to some implementations.
Figure 5:
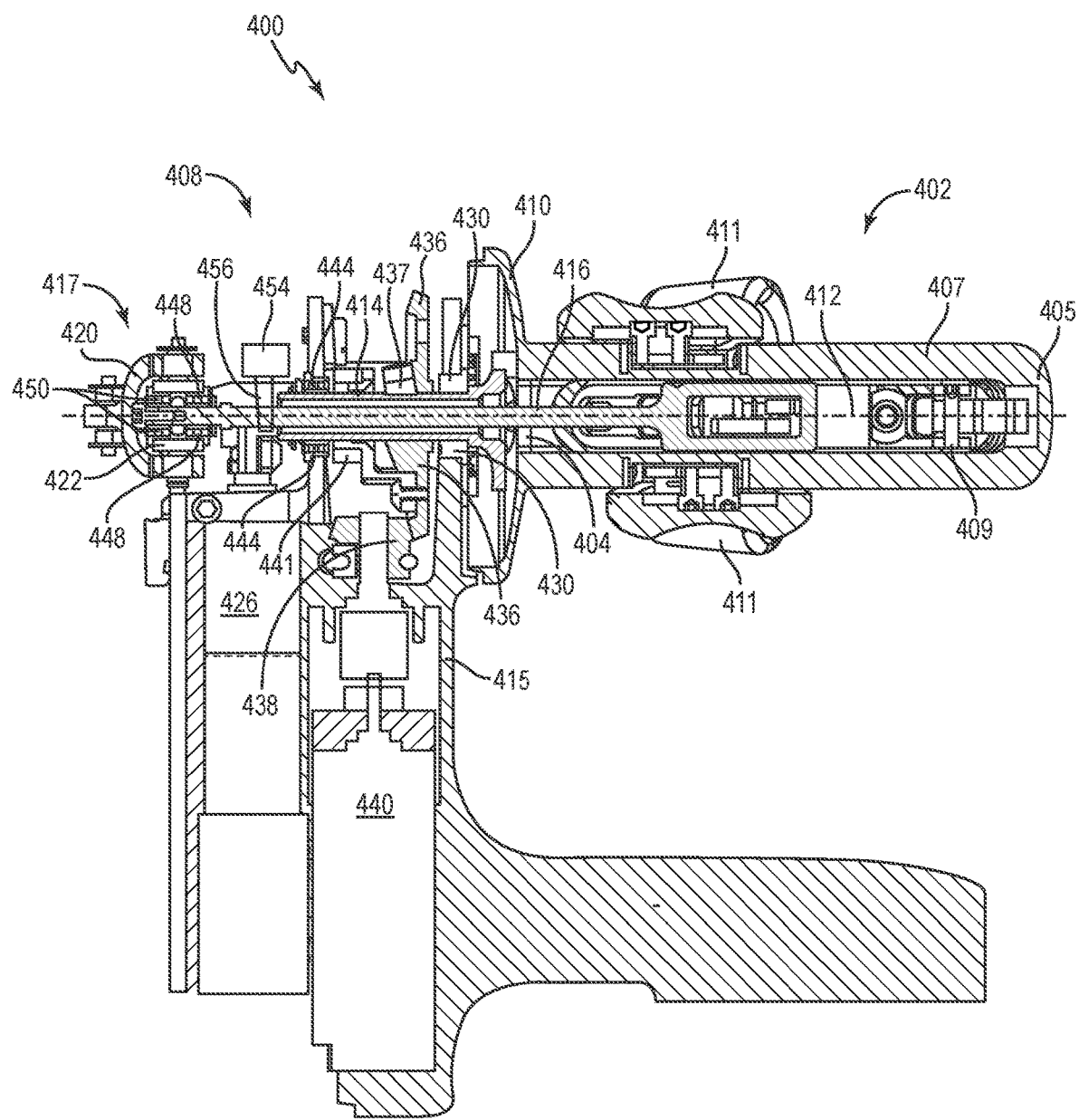

FIG. 4 is a top sectional view of an example implementation of a device portion 400 of a control input device including one or more features described herein, according to some implementations. FIG. 5 is a side elevational view of example device portion 400. In some implementations, device portion 400 can be implemented as device portion 300 in the control input device described above with respect to FIG. 3, or can be included in a different control input device.

Device portion 400 includes a handle 402 coupled to a support structure 408, which in some implementations can be similar to handle 302 and base member housing 309 as described for FIG. 3.

Handle 402 includes a first end (proximal end) 404, a second end (distal end) 405 opposite the first end, and a central axis 412 defined between the first and second ends. A central portion 407 of handle 402 can extend between the proximal end 404 and distal end 405. Handle 402 can be rotated about central axis 412 in a roll degree of freedom with respect to the support structure 408. In some implementations, handle 402 can include grip members 406 that are rotationally coupled to a central portion 407 that extends along the central axis 412, similarly as grip members 306 of FIG. 3. Grip members 406 can be rotatably coupled to central portion 407 by rotary couplings 409. In some implementations, central portion 407 can be positioned between at least two fingers of a hand during grip of the handle by the hand, similarly as described for FIG. 3. Grip members 406 can be at least partially electrically conductive, isolated from electrical ground, and included in an antenna for the capacitive sensor as described below.

Finger loops 411 can be coupled to grip members 406 and can be used to secure a user's fingers to the associated grip member 406. In some implementations, finger loops 411 can be coupled to grip member portions 413 that are coupled to grip members 406. In some implementations, finger loops 411 and/or grip member portions 413 can be made at least partially electrically conductive. For example, particles of electrically conductive material (e.g., particles of carbon fiber or a metal) can be dispersed throughout a material of the finger loops 411 such as silicone rubber or other flexible material used for the finger loops, in such a concentration as to allow the finger loops to be at least partially electrically conductive. In some implementations, grip member portions 413 can be made of an electrically conductive material, or can be made of a more insulative material (e.g., plastic) and include conductive particles similarly to finger loops 411.

Handle 402 can also include a plate 410 and a tube 414 that that rotate about axis 412. Plate 410 is rigidly coupled to tube 414 that extends into support structure 408. Plate 410 can be part of the antenna formed by handle 402, as described below.

Support structure 408 is rotationally coupled to handle 402, and handle 402 rotates about axis 412 with respect to support structure 408. Support structure 408 can have a variety of shapes in various configurations. In an example implementation, support structure 408 is mechanically coupled to a ground such that handle 402 is mechanically grounded, e.g., via one or more links (such as links 324 and 326 as described above). In other implementations, support structure 408 is mechanically ungrounded and can be moved freely in a working environment. Support structure 408 is electrically grounded. For example, chassis 415 is electrically grounded.

Support structure 408 includes a tube 414 (or other cylindrical member) that rotates about axis 412 with respect to chassis 415 of the support structure 408. Tube 414 is coupled to a bearing 430 that enables the rotation of tube 414. A shaft 416 is coupled to handle 402 and extends through an inner bore of tube 414 to a drive mechanism 417 provided in support structure 408. Shaft 416 is translatably (e.g., slidably) coupled to tube 414. In various implementations, shaft 416 can be in contact with tube 414, or can be separated and not in contact with tube 414. Tube 414, shaft 416, and plate 410 can be isolated from electrical ground as described below. In some implementations, shaft 416 can be omitted, e.g., tube 414 can be a shaft having a solid interior.

Drive mechanism 417 can convert rotational forces output by a rotary actuator 426 (shown in FIG. 5) to linear forces that drive mechanism 417 applies to shaft 416. In this example, drive mechanism 417 includes rotatably-coupled links 418 and 420. For example, link 418 of drive mechanism 417 is coupled to actuator 426 and transmits rotational forces from rotary actuator 426 to link 420 that is rotationally coupled to link 418 and rotationally coupled to carriage 422. Carriage 422 is rigidly coupled to shaft 416 and translates along a rail 424, and thus translates shaft 416 linearly along axis 412 through tube 414 as carriage 422 slides along the rail. In some implementations, shaft 416 moves a linkage 428 in handle 402 that includes two members rotatably coupled to shaft 416 at rotary couplings 429 and each rotatably coupled to a grip member 406 at a rotary coupling 431. Shaft 416 is driven linearly by actuator 426 to rotate the grip members 406 about their axes of rotation via linkage 428.

Other drive mechanisms can alternatively be used in device portion 400 instead of drive mechanism 417 to transmit forces from an actuator to shaft 416 to translate shaft 416 linearly along axis 412. For example, links having other dimensions or configurations can be used. In other examples, a capstan drive mechanism, gear mechanism, ballscrew mechanism, or other mechanism can be used.

A rotary bearing 430 is coupled between chassis 415 and tube 414. Bearing 430 allows tube 414 to rotate about axis 412 with respect to chassis 415. In some examples, bearing 430 is a ball bearing having an inner ring, an outer ring, and multiple balls positioned between these rings, and the inner ring and outer ring can rotate with respect to each other. For example, tube 414 can be rigidly coupled to the inner ring and chassis 415 can be rigidly coupled to the outer ring. Some example implementations of a ball bearing are described with reference to FIG. 7. In some implementations, rotary bearing 430 can be or include other types of bearings, e.g., roller bearings such as cylindrical roller bearings, etc.

In some implementations, rotary bearing 430 includes an insulator that electrically isolates tube 414 and handle 402 at bearing 430 from the support structure 408 (e.g., chassis 415) that is coupled to electrical ground. In some examples, the insulator can be an insulating surface or layer that is provided on a surface of the bearing, or a component of the bearing that is made of an insulating material. Some examples of an insulator for a bearing are described below with reference to FIG. 7.

A drive mechanism can be provided between tube 414 and an actuator 440 to transmit force from an actuator to rotate tube 414. In this example, the drive mechanism includes a gear mechanism that includes gear 436 and gear 438 (see FIG. 5). Gear 436 can be rigidly coupled to tube 414 at the central aperture or hub of gear 436. Gear 436 is used to drive the rotation of tube 414 about axis 412 with reference to chassis 415. Gear 436, shaft 416, plate 410, and other components of handle 402 are coupled to tube 414 and rotate with tube 414. In some implementations, gear 436 can be rigidly coupled to a clamp 437 (see FIGS. 5 and 6) that further secures the gear 436 to tube 414. Gear 436 engages with gear 438 that is coupled to an actuator 440 (shown in FIG. 5). Actuator 440 can be a motor or other active actuator that has a housing coupled to chassis 415 and that outputs a rotary force on a rotating shaft of the actuator. The rotating shaft is rigidly coupled to gear 438. Gear 438 engages with gear 436 via gear teeth provided on an engaging surface of gear 438 and gear teeth provided on an engaging surface of gear 436. Rotation of gear 438 by actuator 414 causes rotation of gear 436, which in turn rotates tube 414, shaft 416, plate 410, and handle 402 (including grip members 406) about axis 412 with reference to chassis 415.

Other gear mechanisms can be used in other implementations, e.g., a mechanism including multiple gears. Other drive mechanisms can alternatively be used in device portion 400 instead of the gear mechanism described above to transmit forces from an actuator to tube 414 to rotate tube 414 about axis 412. For example, a capstan drive mechanism, belt and pulley mechanism, or other mechanism can be used having drive elements similar to gears which can include an insulator similarly as described herein.

In some implementations, one or more control input sensors (e.g., roll sensors) can be coupled to the actuator 440 and detect the orientation of gear 436. The orientation of gear 436 indicates the roll (rotary) orientation of the handle 402 about axis 412. For example, a rotary encoder can be coupled to the actuator shaft and included in housing of actuator 440. The roll sensor can send signals describing sensed orientations and/or motion of the handle 402 to a control unit. In some modes or implementations, the control unit can provide control signals to the manipulator system 104. In some implementations, other sensors can also or alternatively be used to detect rotation of handle 402 about axis 412. For example, an encoder 441 (e.g., including an encoder magnet) can be positioned around tube 414 and sense the orientation of tube 414 and/or gear 436 about axis 412. Supports 443 can be coupled to gear 436 to hold the encoder 441 and can contact tube 414 in some implementations. In various implementations, a magnet of the encoder 441 is insulative, and/or supports 443 can be made of an insulating material, e.g., plastic, to isolate tube 414 from gear 436.

In some implementations, gear 436 includes an insulator that electrically isolates tube 414 and handle 402 through gear 436 from the support structure 408 (e.g., chassis 415) that is coupled to electrical ground. In some examples, the insulator can be an insulating surface or layer that is provided on a surface of the gear, or a component of the gear that is made of an insulating material. Some examples of an insulator for a gear are described below with reference to FIGS. 8-10.

A rotary bearing 444 can be coupled between chassis 415 and tube 414 on the opposite side of gear 436 to rotary bearing 430. Similar to bearing 430, bearing 444 allows tube 414 to rotate about axis 412 with respect to chassis 415. In some examples, bearing 444 is a ball bearing having an inner ring, an outer ring, and multiple balls positioned between the rings, and the inner ring and outer ring can rotate with respect to each other. For example, tube 414 can be rigidly coupled to the inner ring and chassis 415 can be rigidly coupled to the outer ring. Some example implementations of a ball bearing are described with reference to FIG. 7. In some implementations, rotary bearing 430 can be or include other types of bearings similarly as described for bearing 430.

In some implementations, rotary bearing 444 includes an insulator that electrically isolates tube 414 and handle 402 at bearing 444 from the support structure 408 (e.g., chassis 415) that is coupled to electrical ground. In some examples, the insulator can be an insulating surface or layer that is provided on a surface of the bearing, or a component of the bearing made of an insulating material. Some examples of an insulator for a bearing are described below with reference to FIG. 7.

Drive mechanism 417 is rotationally coupled to shaft 416 via a rotary bearings 448 and 450. Bearings 448 and 450 are coupled between carriage 422 and shaft 416 on the sides of carriage 422 of drive mechanism 417. In some examples, bearings 448 and 450 can be ball bearings similar to bearing 430 described above. For example, shaft 416 can be rigidly coupled to inner rings and chassis 415 can be rigidly coupled to outer rings of the bearings. Bearings 448 and 450 allow shaft 416 to rotate about axis 412 with respect to carriage 422. Shaft 416 can rotate relative to carriage 422. Shaft 416 can be prevented from translating along axis 412 relative to carriage 422, e.g., by stops or other features of carriage 422 along axis 412. In various implementations, rotary bearings 448 and 450 can be ball bearings as described above or other types of bearings similarly as described for bearing 430. In some implementations, shaft 416 and carriage 422 can be pre-loaded, e.g., with a wave spring 451 and/or a screw 453.

In some implementations, rotary bearings 448 and 450 each include an insulator that electrically isolates shaft 416 and handle 402 at bearings 448 and 450 from electrical ground provided via drive mechanism 417, actuator 426, and support structure 408 (e.g., chassis 415). In some examples, the insulator can be an insulative surface or layer that is provided on a surface of the bearings 448 and 450, or a component of the bearing made of an insulative material. Some examples of an insulator for a bearing are described below with reference to FIG. 7.

In some implementations, one or more links of drive mechanism 417 can include an insulator. For example, an internal bore of the carriage 422, that connects to bearings 448 and 450, can be anodized or a different type of insulating layer can be applied thereto, which electrically isolates the drive mechanism 417 and actuator 426 from the shaft 416.

In some implementations, a rotary electrical connector 454 (shown in FIGS. 5 and 6) is coupled to shaft 416. Rotary electrical connector 454 provides an electrical connection between shaft 416 and a capacitive sensor circuit. Some examples of the capacitive sensor circuit are described below with reference to FIG. 11. Rotary electrical connector 454, for example, can be a slip ring device that includes one or more contact leads 456 that are physically pressed against shaft 416 (e.g., by a spring) and allows shaft 416 to continuously rotate about axis 412 while maintaining an electrical connection from shaft 416 to connector 454. In some implementations, rotary electrical connector 454 can be coupled to tube 414 instead of shaft 416, or to another rotating component of the handle assembly that rotates about axis 412 (including shaft 416, tube 414, plate 410, and handle 402).

The insulation features of bearings 430, 444, 448, and 450 and the insulation features of the gear mechanism that includes gears 436 and 438 allow the handle assembly (including handle 402, shaft 416, and tube 414, where handle 402 includes central portion 407, grip members 406, and plate 410) to be electrically isolated from electrical ground. For example, bearings 430, 444, 448, and 450 and gear 436 can be the only points of physical contact between the handle assembly and grounded components such as chassis 415, actuators 426 and 440, and drive mechanism 417. This allows the handle assembly, including handle 402, to operate as an antenna for the capacitive sensor circuit that can sense a presence of a user's hand as described herein. In some implementations, the handle assembly can include other components that can similarly be isolated from electrical ground. In some implementations, different or additional components of device portion 400 can be isolated from electrical ground and operate as an antenna for the capacitive sensor circuit.

Figure 6:
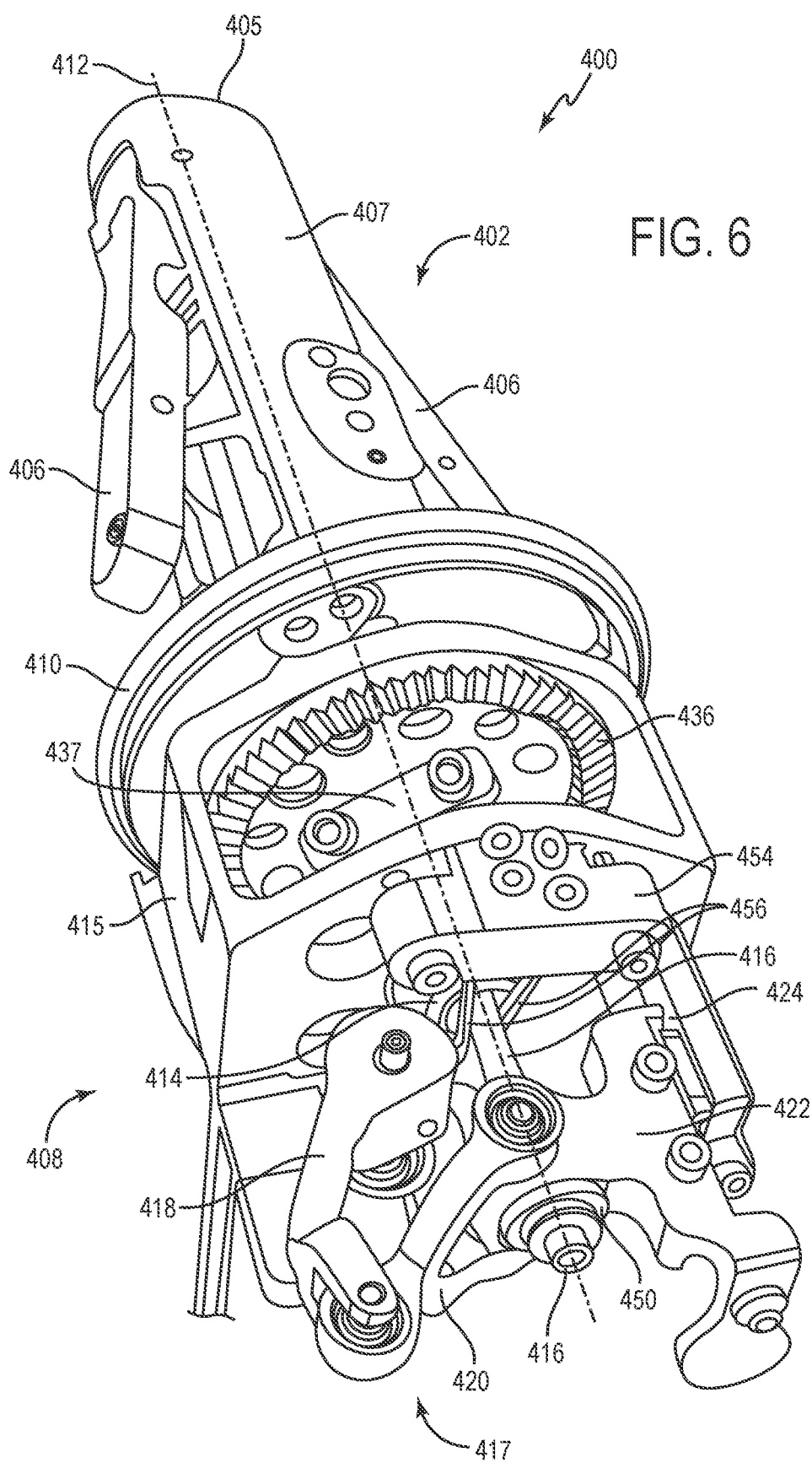

FIG. 6 is a perspective view of the example device portion 400 of FIG. 4, with corresponding components labelled similarly. In this view, finger loops 411 and grip member portions 413 are not shown on grip members 406. In some implementations, rotary electrical connector 454 includes two contacts 456 that are spring biased or otherwise held in place in contact with two sides of shaft 416 to maintain an electrical connection between contacts 456 and shaft 416. Electrical wires or cables such as wire 602 can be routed from rotary electrical connector 454 to the capacitive sensor circuit to communicate signals between these components and to the handle assembly operating as an antenna for the capacitive sensor circuit.

Figure 7:
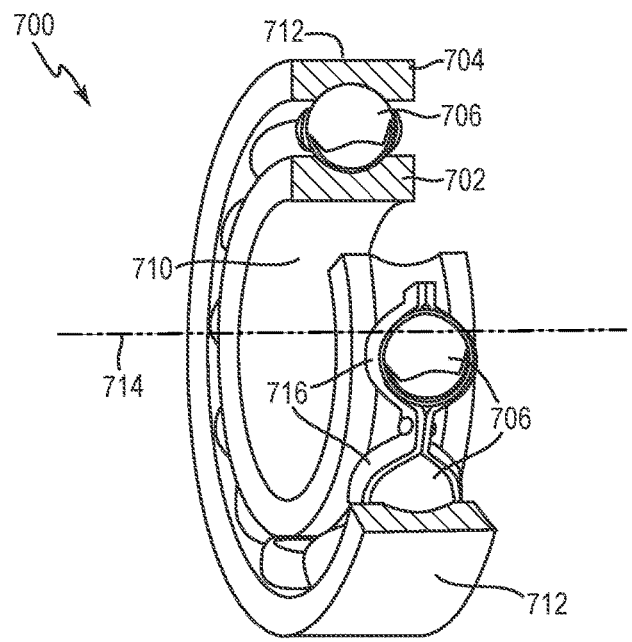
FIG. 7 is a perspective sectional view of an example ball bearing that can be used in a control input device including one or more features described herein, according to some implementations.

FIG. 7 is a perspective sectional view of an example ball bearing 700 which can be used to isolate components in a control input device, according to some implementations. For example, in some implementations, ball bearing 700 can be used as rotary bearing 430, 444, 448, and/or 450 of FIGS. 4-6 to allow rotation of tube 414 or shaft 416 about axis 412.

Ball bearing 700 includes an inner ring (e.g., race) 702, an outer ring (e.g., race) 704, and multiple balls 706. Balls 706 are positioned between inner ring 702 and outer ring 704 and contact inner ring 702 at a groove of the inner ring 702 and contact outer ring 704 at a groove of the outer ring 704. Balls 706 rotate between the inner ring 702 and outer ring 704 to enable one ring to rotate about the axis 714 of the bearing with respect to the other ring. In some implementations, a cage 716 can be provided around balls 706 to prevent balls 706 from contacting each other as a result of rolling.

In some implementations, ball bearing 700 can include an insulator that electrically isolates one element coupled to (e.g., contacting) bearing 700 from another element coupled to (e.g., contacting) bearing 700. In some examples, the insulator can be an insulative material (e.g., layer) that is provided on an inner surface 710 of the bearing 700 and/or outer surface 712 of the bearing 700. In some examples, an insulative material can be sprayed on outer ring 704, including outer surface 712, such as aluminum oxide powder or other insulating material. In some implementations, the insulative material can be applied to inner surface 710 of inner ring 702 or other surfaces of rings 702 and/or 704, e.g., surfaces that contact balls 706.

In another example, one or more surfaces of ball bearing 700 can be anodized to form an insulative anodized metal layer on these surfaces (if the surfaces are made of a material that can be anodized), e.g., on inner surface 710, outer surface 712, and/or on other surfaces of inner ring 702 and/or outer ring 704. In another example, either or both rings 702 and 704 of bearing 700 can be coated or wrapped in an insulative sleeve (e.g., nylon or plastic sleeve) or other insulative material, e.g., insulative tape.

In some implementations, the insulator electrically isolates a first bearing portion of bearing 700 from a second bearing portion of bearing 700, which isolates an element that is coupled to (e.g., contacting) the first bearing portion from an element that is coupled to (e.g., contacting) the second bearing portion. In some examples, the insulator can be a portion of ball bearing 700 that is made of an insulative material. For example, balls 706 can be made out of an insulative material such as ceramic, plastic, etc. Thus, inner ring 702 and outer ring 704 are electrically isolated from each other. In some implementations, inner ring 702 and/or outer ring 704 can be made of an insulative material, e.g., ceramic, plastic, etc., in addition to or alternative to balls 706 being made out of an insulative material.

In various implementations, a combination of one or more of these types of insulators can be used, e.g., an insulative surface on one or more rings 702 and/or 704, and components such as balls 706 or ring(s) made of an insulative material.

The insulator provided in ball bearing 700 allows an element (e.g., a component of the control input device) coupled to inner ring 702 to be electrically isolated from an element (e.g., another component) coupled to outer ring 704. For example, as shown in FIG. 4, bearing 430 can be coupled between chassis 415 and tube 414, where an outer ring of bearing 430 is coupled to chassis 415 and an inner ring of bearing 430 is coupled to tube 414. The insulator provided in bearing 430 causes chassis 415 to be electrically isolated, at bearing 430, from tube 414 and the other components of the handle assembly including handle 402. In various implementations, a similar configuration can be provided for bearings 444, 448, and/or 450.

Figure 8:
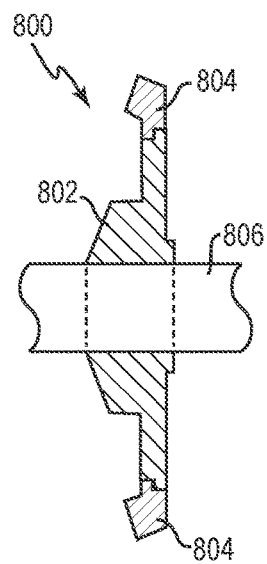
FIGS. 8-10 are side sectional views of a gear or gear assembly that can be used in a control input device including one or more features described herein, according to some implementations.

FIG. 8 is a sectional side view of an example gear 800 which can be used to isolate components in a control input device, according to some implementations. For example, gear 800 can be used as gear 436 of FIGS. 4-6 that transmits force from actuator 440 to tube 414 about axis 412.

Gear 800 includes an electrically conductive portion 802 and an electrically insulative portion 804. Conductive portion 802 can be made of a metal (such as aluminum) or other electrically conductive material, and is coupled to tube 806 that extends through a hub or aperture of conductive portion 802. For example, tube 806 can be tube 414 of FIGS. 4-6. Conductive portion 802 can be rigidly coupled to tube 806 to cause tube 806 to rotate when gear 800 rotates. In some implementations, conductive portion 802 of gear 800 can be coupled to a clamp (not shown) that secures gear 800 to tube 806, where the clamp can be made of conductive material.

Insulative portion 804 can be rigidly coupled to conductive portion 802. For example, insulative portion 804 can be an outer ring or other outer portion of gear 800 that includes the gear teeth of gear 800. Insulating portion 804 can be made of plastic or other electrically insulative material.

The insulator provided in gear 800 allows a component coupled to the hub of gear 800, such as tube 806, be electrically isolated from a second gear coupled to insulative portion (and isolated from other components coupled to the second gear). For example, as shown in FIG. 5, gear 436 can be coupled between gear 438 and tube 414, where an insulative portion of gear 436 (similar to insulating portion 804) is coupled to gear 438 and a conductive portion (similar to conductive portion 802) is coupled to tube 414. The insulative portion of gear 436 causes gear 438 and actuator 440 to be electrically isolated, via gear 436, from tube 414 and the other components of the handle assembly including handle 402.

In other implementations, portion 802 can be an electrically insulative portion and portion 804 can be an electrically conductive portion, and/or the clamp can be made of an insulative material.

Figure 9:
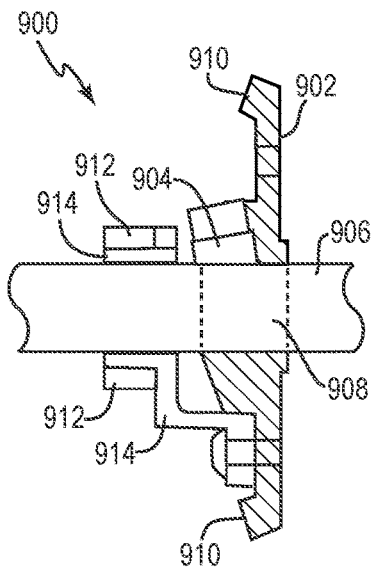

FIG. 9 is a sectional side view of an example gear assembly 900 which can be used in a control input device to isolate components of a capacitive sensor antenna, according to some implementations. For example, in some implementations, gear assembly 900 can be used as gear 436 and clamp 437 of FIGS. 4-6 that transmits force from actuator 440 to tube 414 about axis 412.

Gear assembly 900 includes a gear 902 that can be made of an electrically conductive material, e.g., a metal such as aluminum. Gear 902 is rigidly coupled to a tube 906 that extends through a hub or aperture of gear 902. In this example, gear 902 is coupled to clamp 904 that secures gear 902 to tube 906. In some examples, gear 902 can be gear 436 and clamp 904 can be clamp 437 of FIGS. 4-6. Gear 902 and clamp 904 can be rigidly coupled to tube 906 to cause tube 906 to rotate when gear 902 rotates. In some examples, tube 906 can be tube 414 of FIGS. 4-6. In some implementations, an encoder 912 can be positioned around tube 906 and sense the orientation of tube 906 and/or gear 902 about an axis. In this example, supports 914 are coupled to gear 902, contact tube 906, and hold the encoder 912. For example, encoder 912 can be encoder 441 and supports 914 can be supports 443 of FIGS. 4-6.

In this example, gear 902 includes an insulator that is an anodized surface 908 of the hub or interior of the aperture extending through gear 902. An anodized surface 908 contacts tube 906 and thus provides electrical isolation between gear 902 and tube 906. In implementations including clamp 904, the surfaces of clamp 904 that contact tube 906 can also be anodized to provide electrical isolation between clamp 904 and tube 906. Or, clamp 904 can be made of an insulative material, e.g., plastic. In some implementations, supports 914 can be made of an insulative material, e.g., plastic, to isolate tube 906 from gear 902.

In some implementations, tube 906 can include an insulative surface or layer instead of, or in addition to, gear 902 and clamp 904 including insulative surfaces, causing electrical isolation between tube 906 and gear assembly 900. For example, a portion of the cylindrical surface of tube 414 that comes into contact with gear 902 and clamp 904 can be anodized or coated with a layer of an insulative material. In some implementations, tube 906 may be a shaft that translates through gear 902, and tube 906 can include an insulative surface over the surface portions that may translate into contact with gear 902 and/or clamp 904.

In some implementations, the surfaces of gear teeth 910 of gear 902 are an insulator instead of or in addition to the other insulators for gear assembly 900 described above. For example, the surfaces of all the gear teeth 910 of gear 902 can be anodized to provide an insulative layer that contacts a second gear (e.g., gear 438 of FIGS. 4-6). This feature causes electrical isolation between gear 902 and the second gear that is connected to electrical ground. In some implementations, a different insulative layer can be applied to gear teeth 910, such as layer of aluminum oxide or other insulative material. In some implementations, the second gear can also or alternatively include an insulative layer applied to its gear teeth to provide electrical isolation between the second gear and gear 902, e.g., an anodized layer, an aluminum oxide layer, or other insulative layer applied on its gear teeth.

Any of these insulators causes gear 438 and actuator 440 to be electrically isolated, via gear 436, from tube 414 and the other components of the handle assembly including handle 402.

Figure 10:
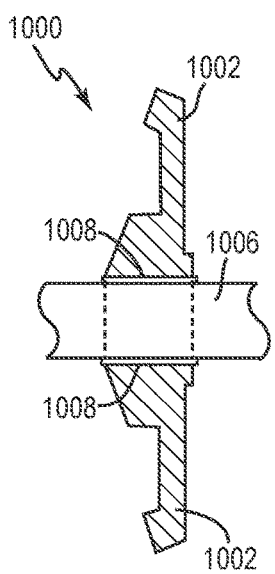

FIG. 10 is a sectional side view of an example gear assembly 1000 which can be used in a control input device to isolate components of a capacitive sensor antenna, according to some implementations. For example, in some implementations, gear assembly 1000 can be used as gear 436 and clamp 437 of FIGS. 4-6 that transmits force from actuator 440 to tube 414 about axis 412.

Gear assembly 1000 includes a gear 1002 that can be made of an electrically conductive material, e.g., a metal such as aluminum. Gear 1002 is rigidly coupled to a tube 1006 that extends through a hub or aperture in gear 1002. In some implementations, gear 1002 can be coupled to a clamp (not shown) that secures gear 1002 to tube 1006, similarly as described for FIG. 8. In some examples, gear 1002 can be gear 436 and the clamp can be clamp 437 of FIGS. 4-6. Gear 1002 (and clamp, if any) can be rigidly coupled to tube 1006 to cause tube 1006 to rotate when gear 1002 rotates. In some examples, tube 1006 can be tube 414 of FIGS. 4-6.

In this example, gear 1002 includes a sleeve 1008 that is provided on the interior surface of the hub or aperture of gear 1002. Sleeve 1008 is made of an electrically insulative (non-conductive) material, e.g., a ceramic material or plastic, to provide an insulative layer between gear 1002 and tube 1006. An insulator can also be applied to surfaces of the clamp, if present, that contacts tube 1006, or the clamp can be made of insulative material. In some implementations, a sleeve or layer similar to sleeve 1008 can be alternatively attached to tube 1006 to isolate the tube from gear 1002 and/or a clamp. With respect to FIG. 4, any of these insulators causes gear 438 and actuator 440 to be electrically isolated, via gear 436, from tube 414 and the other components of the handle assembly including handle 402.

Figure 11:
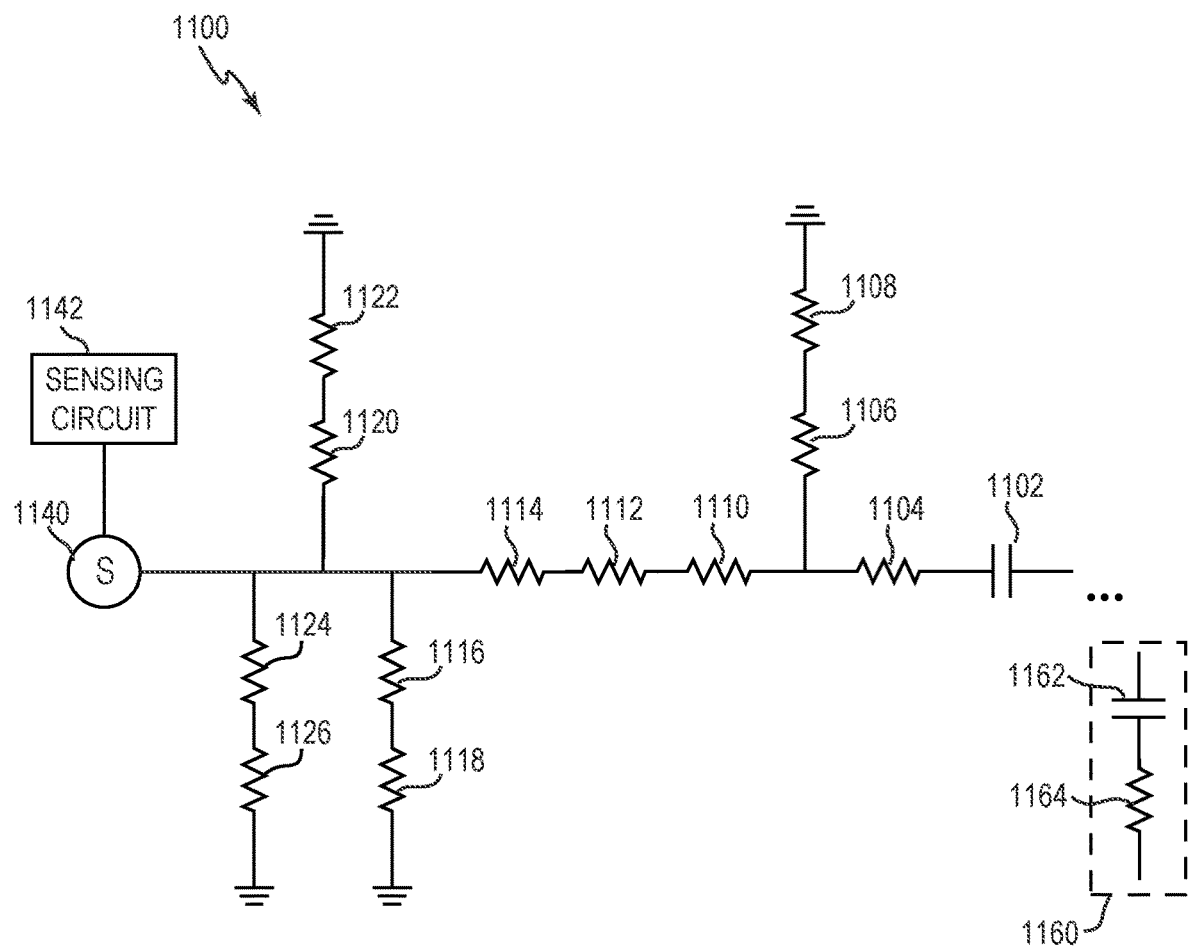
FIG. 11 is a diagrammatic illustration of an example circuit that provides capacitive sensing to detect a presence of a user for a control input device, according to some implementations.

FIG. 11 is a diagrammatic illustration of an example circuit 1100 that provides capacitive sensing to detect a presence of a user for a control input device, according to some implementations. For example, circuit 1100 can be used with device portion 300 of FIG. 3 and/or device portion 400 of FIG. 4 of a control input device as described above. In this example, circuit features are referenced to components described above for device portion 400 of FIG. 4.

Circuit 1100 is a schematic representation of components of a control input device to provide a capacitive sensor that includes a capacitive sensor circuit and can include an antenna for the capacitive sensor circuit. The capacitive sensor can sense capacitance of the antenna (with reference to electrical ground) and can determine changes in capacitance of the antenna based on changes in its surroundings, such as a grounded object moving into sensing range of the capacitive sensor. For example, a handle assembly of the control input device can act as the sensor antenna and includes a handle of the control input device, such as handle 402 shown in FIG. 4, that is contacted and grasped by the user during operation of the control input device. The handle assembly can also include a tube and/or a shaft that extends into a chassis, as described in examples herein, to which the capacitive sensor circuit is coupled. The capacitive sensor can detect a presence of an object, such as a user's hand, within the sensing field of the capacitive sensor by detecting the antenna capacitance as changed by the presence of the object. In some implementations, the presence can be a contact between antenna and object, e.g., during operation of the control input device by the hand, or the presence can be the object located near to the antenna, e.g., within a sensing range of the sensor, when the object does not contact the control input device.

In some implementations, the capacitive sensor can measure a capacitance of a capacitor formed by the antenna and electrical ground. The capacitance is changed by the insertion of a nearby object that has its own capacitance (such as a user's hand). The antenna is isolated from electrical ground to allow the capacitor to electrical ground to be formed and its capacitance measured. For example, the handle of the control input device is isolated using electrical isolation elements (e.g., insulated components) as described herein, each element contributing to the isolation of the handle from electrical ground. The detection of the user's hand can be limited to handle 402 and/or a targeted subset of components of the device portion 400 near to locations where the user grasps handle 402. If the antenna is connected to other components, the sensor circuit may not be able to distinguish a user touching those components compared to touching the handle 402. Furthermore, a chassis such as support structure 408 is typically electrically grounded for electromagnetic compatibility to reduce its electromagnetic interference. If the antenna is connected to electrically grounded components of support structure 408, the capacitive sensor circuit may not operate properly. In some implementations, the antenna can be located a distance from electrically grounded components of the control input device, if closeby electrically grounded components affect the sensing capability of the capacitive sensor to a large degree.

Circuit 1100 includes a capacitance 1102 that represents the capacitance of the handle (e.g., base capacitance) and all things connected to it electrically that have not been insulated from electrical ground, such as grip members that are contacted by a user's fingers to operate the control input device. The capacitance of the device portion 400 may be distributed throughout the various components of the handle 402 and device portion 400, but the capacitance value of non-handle components is relatively small.

In general, electrical resistances shown in circuit 1100 can be controlled to cause handle 402 to operate as an effective antenna. For example, some resistances can be increased to provide insulation from electrical ground, and some resistances can be decreased to provide conductivity between components and extend the antenna of the sensor circuit to more surfaces that are likely to be contacted by a user operating the control input device. In some examples, resistances in series between capacitance 1102 and sensor circuit 1142 can be reduced to provide more conductivity, and resistances in parallel paths to electrical ground can be increased to provide more electrical insulation from electrical ground to the handle antenna.

Resistance 1104 is electrically coupled to capacitance 1102 and represents an electrical resistance of one or more finger loops provided on one or more grip members of the handle of the control input device. The finger loops may be in contact with fingers of the user during operation of the control input device. For example, resistance 1104 can be provided by finger loops 411 of device portion 400 of FIG. 4. In some implementations, resistance 1104 is desired to be minimized and finger loops can be made at least partially electrically conductive. This can advantageously extend or increase the amount of surfaces of the antenna of the handle used for capacitive sensing, e.g., provide additional sensed surfaces that will likely be touched by a user operating the control input device (or that may be very close to the user's hand) and thus allow more robust sensing of the user. For example, particles of conductive material (e.g., particles of carbon fiber or a metal) can be dispersed throughout a material of the finger loops such as silicone rubber or other material used for the finger loops, in a concentration sufficient to allow the finger loops to be at least partially electrically conductive.

In some implementations, resistance 1104 can also or alternatively include other resistances involving the grip members. For example, resistance 1104 can include electrical resistance between grip members and grip member portions that are connected to the finger loops, e.g., grip member portions 413 of FIG. 4. These grip member portions may be made at least partially electrically conductive (e.g., by being made of a conductive material or including conductive particles) to similarly provide additional user-contact surfaces for the antenna. In another example, resistance 1104 can include electrical resistance provided via rotary couplings between grip members and a central shaft of the control input device, e.g., resistance provided by rotary couplings 431 that connect grip members 406 to linkage 428 of device portion 400, and/or resistance provided by rotary couplings 429 that connect linkage 428 to central shaft 416. In some implementations, these resistances at couplings 429 and 431 can be reduced similarly as described below for rotary coupling 409.

Resistance 1106 is electrically coupled to resistance 1104 and represents electrical resistance provided via one or more rotary bearings coupled to a central shaft of the control input device, where the central shaft is coupled to the handle 402 (e.g., via a linkage such as linkage 428). For example, resistance 1106 can represent electrical resistance provided by rotary bearings 448 and 450 that couple central shaft 416 to drive mechanism 417 of device portion 400. Central shaft 416 has a connection to electrical ground via grounded components of drive mechanism 417.

Resistance 1106 can be increased to isolate the central shaft from electrical ground to allow the handle assembly to be isolated from electrical ground. Insulative resistance 1108 represents electrical resistance added to one or more of the bearings providing resistance 1106 (e.g., bearings 448 and 450) to further isolate the handle assembly from electrical ground. Resistance 1108 can be implemented as insulators in various ways as described herein, e.g., with respect to FIG. 7. For example, surfaces of the bearings 448 and 450 can be anodized and/or an insulating layer can otherwise be applied. In some implementations, central shaft 416 can include an insulator, such as an insulative layer applied to its surfaces that contact the bearings 448 and/or 450. In some examples, such an insulative layer can include an anodized layer and/or other layer of insulative material.

Resistance 1110 is electrically coupled to resistance 1104 and resistance 1106 and represents electrical resistance provided between the grip members and the rotary couplings that couple the grip members to the handle, e.g., resistance between grip members 406 and couplings 409 that couple the grip members 406 to central portion 407 of handle 402. In some implementations, resistance 1110 can include contact resistance. Resistance 1110 can be reduced to increase conductivity of the couplings 409. For example, insulative material (e.g., anodized layer or other insulative layer) can be reduced or removed from the couplings 409 (e.g., the inside of the bore of coupling 409 is not anodized) and/or from a contacting surface of the grip members. In some implementations, electrically conductive material (e.g., conductive grease) can be applied to surfaces of the couplings 409 and/or to the contacting surface of the grip members.

Resistance 1112 is electrically coupled to resistance 1110 and represents electrical resistance between the handle of the control input device and the couplings connected to the grip members. For example, resistance 1112 can be between handle 402 (e.g., central portion 407) and rotary couplings 409. In some implementations, resistance 1112 can include contact resistance. Resistance 1112 can be reduced to increase conductivity of the handle as an antenna. For example, reducing resistances 1110 and 1112 extends or enhances sensitivity of antenna sensing surfaces from central portion 407 of the handle 402 to grip members 406 of handle 402 via coupling 409. For example, electrically insulative material can be removed from the coupling and/or from a contacting surface of the handle, and/or electrically conductive material can be applied to the coupling and/or to a surface of the handle that contacts the coupling, similarly as described for resistance 1110 as described above.

Resistance 1114 is electrically coupled to resistance 1112 and represents electrical contact resistance between the handle of the control input device and a shaft of the handle that extends into a chassis. For example, resistance 1114 can be between handle 402 (e.g., plate 410 of the handle 402) and tube 414. In some implementations, resistance 1114 can include contact resistance. Resistance 1114 can be reduced to increase conductivity of the handle as an antenna, as described above. For example, electrically insulative material can be removed from one or more of the contacting surfaces of plate 410 (and/or other contacting surfaces of handle 402) and/or of tube 414, and/or electrically conductive material can be applied to one or more of these contacting surfaces, similarly as described for resistances 1110 and 1112 as described above.

Bearing resistance 1116 can be electrically coupled to resistance 1114 as shown and represents electrical resistance provided by a bearing that couples a portion of the handle assembly to a component that is coupled to electrical ground. For example, bearing resistance 1116 can be provided by rotary bearing 430 of device portion 400 that is coupled between tube 414 and chassis 415, where chassis 415 is coupled to ground. Bearing resistance 1116 can be increased to isolate electrically grounded portions of the control input device from antenna portions coupled to the bearing, such as the handle assembly including tube 414. Insulative resistance 1118 represents electrical resistance added to this bearing by an insulator to further isolate the handle assembly and tube 414 from electrical ground. Insulative resistance 1118 can be implemented in various ways as described herein, e.g., with respect to FIG. 7.

Gear resistance 1120 can be electrically coupled to resistances 1114 and 1118 as shown and represents electrical resistance provided by a gear that couples a portion of the handle assembly to a component that is coupled to electrical ground. For example, gear resistance 1120 can be provided by gear 436 of device portion 400 that is coupled between tube 414 and gear 438, where gear 438 is coupled to ground. Gear resistance 1120 can be increased to isolate electrically grounded portions from antenna portions coupled to the gear, such as the handle assembly including tube 414. Insulative resistance 1122 represents electrical resistance added to the gear assembly to further isolate the handle assembly from electrical ground. Insulative resistance 1122 can be implemented in various ways as described herein, e.g., with respect to FIGS. 8-10.

Bearing resistance 1124 can be electrically coupled to resistances 1114, 1118, and 1120 as shown and represents electrical resistance provided by a bearing that couples a portion of the handle assembly to a component that is coupled to electrical ground, similarly to resistance 1116. For example, bearing resistance 1124 can be provided by rotary bearing 444 of device portion 400 that is coupled between tube 414 and chassis 415, where chassis 415 is coupled to ground. Bearing resistance 1124 can be increased to isolate electrically grounded portions from antenna portions coupled to the bearing, such as the handle assembly including tube 414. Insulative resistance 1126 represents electrical resistance added to this bearing by an insulator to further isolate the handle assembly from electrical ground. Insulative resistance 1126 can be implemented in various ways as described herein, e.g., with respect to FIG. 7.

Circuit 1100 is a simplification showing particular examples of resistances and connections between components of the control input device. Electrical resistances for other components, as well as contacts and connections between components, of the control input device can be similarly included in circuit 1100 and can be similarly modified for isolation or conductivity as described above.

Connector 1140 is electrically coupled to the antenna and is an electrical connector that connects a capacitive sensor circuit 1142 to the antenna of the capacitive sensor. For example, connector 1140 can be rotary electrical connector 454 of device portion 400 that connects to shaft 416 or other component of the handle assembly used as the antenna, to provide an electrical connection between the capacitive sensor circuit and the handle assembly while allowing the shaft 416 to rotate. In some examples, connector 1140 can be a single-channel slip ring or other signal connector that can communicate signals to a rotating component (e.g., optical signal transmitter and detector).

Capacitive sensor circuit 1142 is connected to the capacitive antenna by connector 1140. Sensor circuit 1142 transmits a signal to the antenna including circuit 1100 and senses the signal that is based on the current electrical properties of the antenna. The presence of an object, such as a user's hand, changes the signal to allow detection of presence of that object in the sensing field of the capacitive sensor. The sensing field can be any surface of the handle assembly, or in some implementations can be a small distance away from any surface of the handle assembly. For example, contact of the user's hand with grip members can be sensed, or contact of a hand with a surface that is not part of the antenna but which is adjacent or very near to a surface of the antenna.

In some examples, a user (e.g., a hand of the user) can be represented by circuit 1160 in FIG. 11, which includes a capacitance 1162 coupled to a resistance 1164. Moving a hand to contact the handle of the control input device, or to be located very near to the handle surface, causes a change from capacitance 1102 to a capacitance that also includes capacitance 1162 of the user. This modifies the signal on the antenna that is sensed by capacitive circuit 1142 to enable detection of the user's hand contacting the handle or coming close to the handle (e.g., within a threshold distance of the surface of the handle).

In some example implementations, capacitive sensor circuit 1142 includes one or more integrated circuits and/or printed circuit boards. In some examples, capacitive sensor circuit 1142 can be implemented using an integrated circuit sensor that includes, for example, one or more of a signal conditioner, analog to digital converter (ADC), math engine to calculate sensed characteristics, etc. For example, sensor circuit 1142 can include a digital output which can send a signal to the antenna, and a digital input that can receive the signal and sense the capacitance of the antenna. In some implementations, the sensor circuit starts an oscillation signal on the antenna as an electrically conductive electrode and measures the frequency of that oscillation signal (or measures a frequency-related characteristic of the oscillation signal, e.g., phase). Detected changes in frequency are proportional to capacitance. For example, a digital output of circuit 1142 can produce a voltage square wave and can be connected to the antenna via an electrical resistance element connected in series. A digital input of circuit 1142 can sense the phase lag of this square wave, where the phase lag is proportional to a resistor-capacitor (RC) time constant of the series resistance and the antenna. If a user's hand contacts the handle, the RC time constant is greatly altered and this new time constant is sensed. One example of sensing a change of signal caused by user contact with the handle is shown with respect to FIG. 12.

In another example, capacitive sensor circuit 1142 can include an inductance-capacitance (LC) oscillator to generate a signal having a frequency based on the inductance and capacitance. The circuit 1142 can sense the frequency of the signal transmitted on the antenna. A user contacting the handle causes a resulting frequency change which is sensed by the circuit 1142, where the change in frequency is proportional to capacitance. In some implementations, an LC oscillator implementation may have an improved sensing rate and range compared to some implementations described above using the RC time constant, with more complex sensor circuitry in some implementations.

Figure 14:
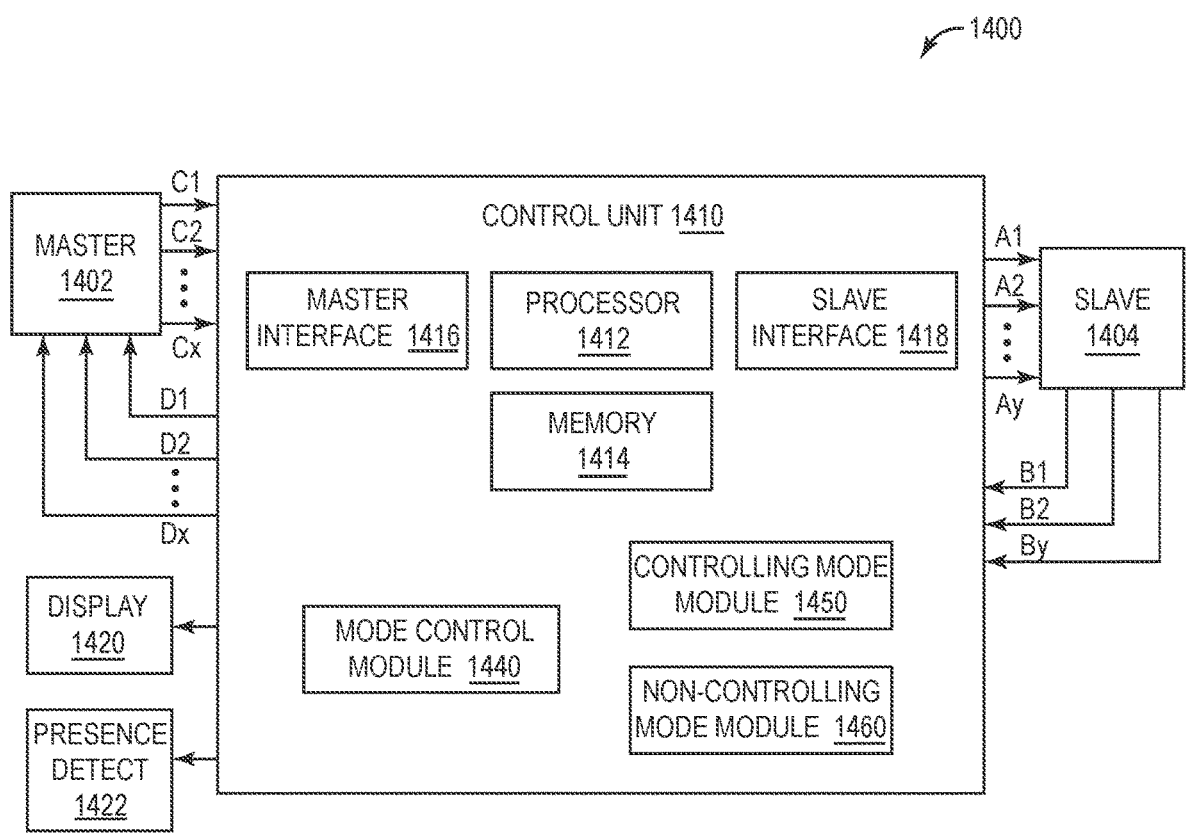
FIG. 14 is a block diagram of an example master-slave system which can be used in one or more implementations described herein.

In some implementations, a received signal can be processed by the sensor circuit and/or by software running on another circuit (e.g., a control unit including a processor 1412 of FIG. 14 or other processor). For example, the measured capacitance can be filtered for noise. In some implementations, one or more detection criteria, such as a threshold for sensed capacitance, can be set such that if the sensed capacitance satisfies the criteria (e.g., is above the threshold), a detection is made and a hand presence event is triggered for the system.

In some implementations, the threshold can be determined based on a particular minimum capacitance that is typically sensed for the presence of the types of object(s) that are intended to be detected. For example, a threshold can be designated such that the sensed capacitance will be at a level that satisfies that threshold (e.g., above the threshold)

when a user hand contacts or is within a particular threshold distance of the antenna handle (e.g., 3 mm). In another example, the threshold can be designated such that the sensed capacitance caused by a contacting hand wearing thick surgical gloves in a dry environment will satisfy the threshold and a detection of user presence will be made for such an object.

For example, detection of a hand presence event by a system such as teleoperated system 100 can be used to change states in response to the detection. In some examples, the change of states can enable a controlling mode to be activated (other conditions may also be required, e.g., user presence also being detected by other presence sensors of a user control system). Similarly, the controlling mode can be exited when the hand presence is no longer detected due to the sensed capacitance not satisfying (e.g., being below) the threshold level.

In some implementations, components of the control input device can be provided with dimensions, shapes, or configurations that tailor the capacitive sensing by the capacitive sensor to particular conditions. For example, a different sensing range or sensitivity (e.g., sensing user presence over a greater range of conditions) can be provided. In some examples, sensitivity and/or shape of a capacitive sensing field can be modified by the placement of one or more electrical ground planes with respect to the antenna, e.g., to reduce sensitivity of particular portions of the control input device. The sensing range of the capacitive sensor can be adjustable in some implementations, e.g., to allow a user to set a particular sensing range. In additional examples, circuit components such as capacitors, resistors, etc. can be added to the antenna to modify sensing properties (e.g., filter noise, etc.). Software control of the parameters and characteristics of the sensor can allow parameters of the sensor (e.g., the capacitance threshold defining a hand detection) to be configurable without adjusting physical characteristics of the control input device.

Mechanically ungrounded control input devices can also use one or more features described herein to sense user presence using the described capacitive sensing. For example, a tethered, mechanically ungrounded control input device or an untethered mechanically ungrounded control input device can use one or more capacitive sensing implementations described herein to sense user contact of a handle portion of the control input device.

Some implementations of mechanically ungrounded or mechanically grounded control input devices can include a circuit and/or mechanism to selectively connect the antenna portion of the control input device to electrical ground. In some examples, a transistor or other electrical switch can be controlled by the sensing circuit, or a mechanical conductive contact can be moved, to shunt an isolated antenna portion to electrical ground. In some examples, this may reduce voltage that has built up on the antenna after a certain amount of time, and/or can help control issues with electromagnetic interference caused by such build up of voltage on the control input device. In some implementations of untethered mechanically ungrounded control input devices, the antenna can be selectively connected to a local (floating) ground element to similarly reduce built-up voltage to a reference level.

Figure 12:
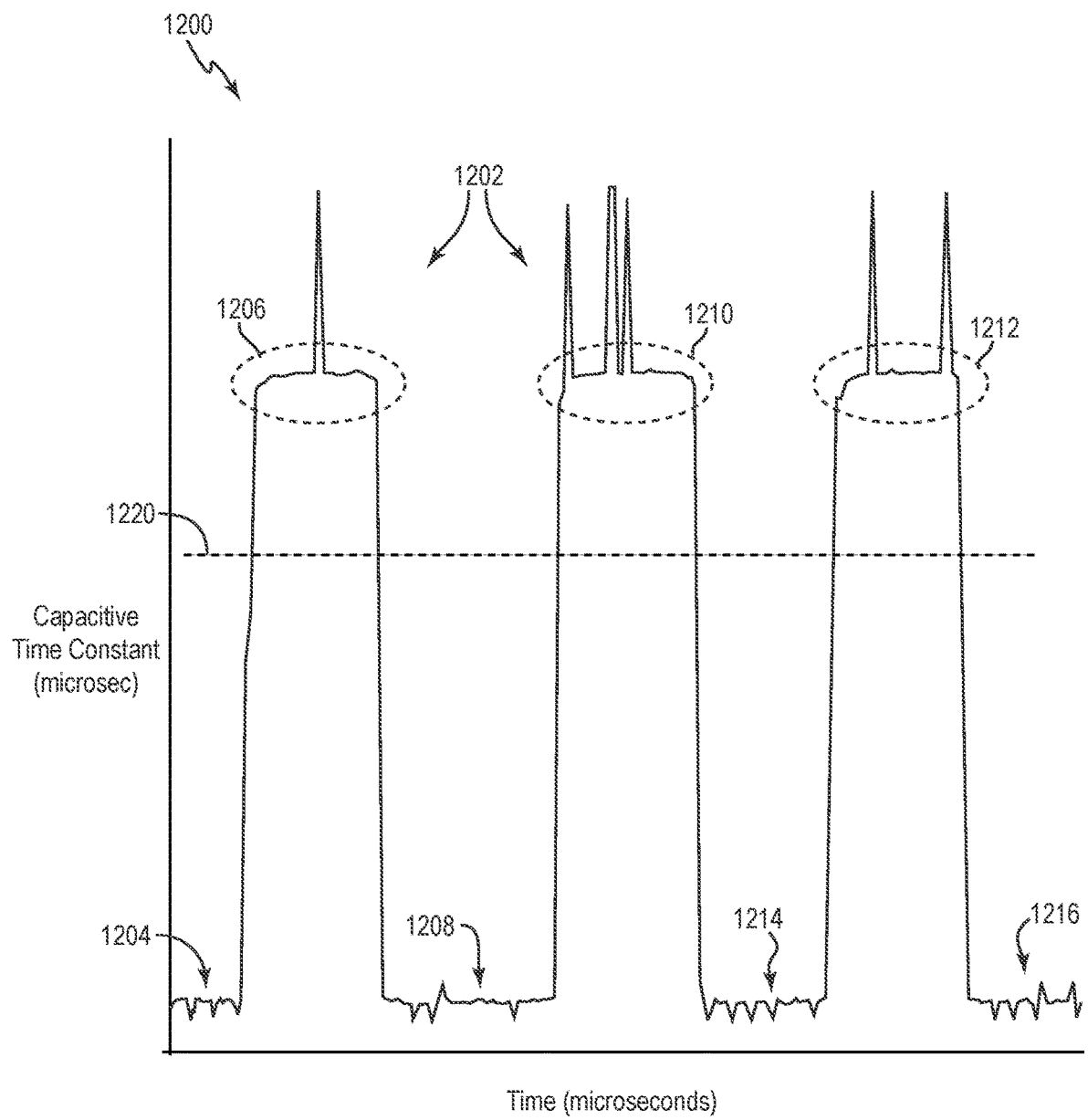
FIG. 12 is a diagrammatic illustration of an example graph showing a waveform sensed by a capacitance sensor, according to some implementations.

FIG. 12 is a diagrammatic illustration of an example graph 1200 showing a waveform 1202 sensed by a capacitance sensor to detect a presence of a user, according to some implementations. Graph 1200 has a vertical axis indicating a capacitive time constant (e.g., in milliseconds) of a signal and a horizontal axis indicating time (e.g., in milliseconds).

Waveform 1202 is an example sensed output of a capacitive sensor circuit. In this example, a square wave has been generated onto the antenna to use in detecting capacitance at the sensor, which allows detection of a presence of a user in the sensing field of the sensor. In some examples, the square wave is generated by an RC circuit of a capacitive sensor circuit such as sensor circuit 1142 as described above with reference to FIG. 11. The phase lag of this square wave can be sensed by the sensor circuit, and the phase lag is proportional to the RC time constant of a series resistance and the antenna of the capacitive sensor. Waveform 1202 indicates the time constant value (vertical scale) that has been sensed over time (horizontal scale) by the sensor circuit.

Section 1204 of the waveform 1202 indicates a low time constant is present, which is related to a base phase lag sensed when no object (such as a hand of a user) is in the sensing field of the capacitive sensor. At section 1206, waveform 1202 goes to a much higher time constant, indicating a large change in phase lag of the square wave that is caused by the presence of an object such as a user's hand. For example, the presence can be contact of the hand on the antenna that is the handle of a control input device, as described herein. The contact of the hand alters the RC time constant and this difference is sensed by the sensor circuit.

Section 1208 of waveform 1202 indicates that the user has removed the hand from the sensing field of the capacitive sensor, causing the time constant to return to its base level. Similarly, the high time constant of sections 1210 and 1212 indicate that the user has contacted the control input device during these times, while the lower time constant of sections 1214 and 1216 indicate that the user has removed contact during these times. The lower level of sections 1204, 1214, and 1216 can be below a designated threshold level 1220, which indicates to a control unit of the system that no user presence is detected. The high level of sections 1206, 1210, and 1212 can be above the designated threshold 1220, which indicates to a control unit of the system that user presence is detected at the control input device.

Other sensor circuits can be used to provide similar or corresponding waveforms. For example, an LC oscillator can be used to sense a resultant frequency change proportionate to capacitance, as described above.

Figure 13:
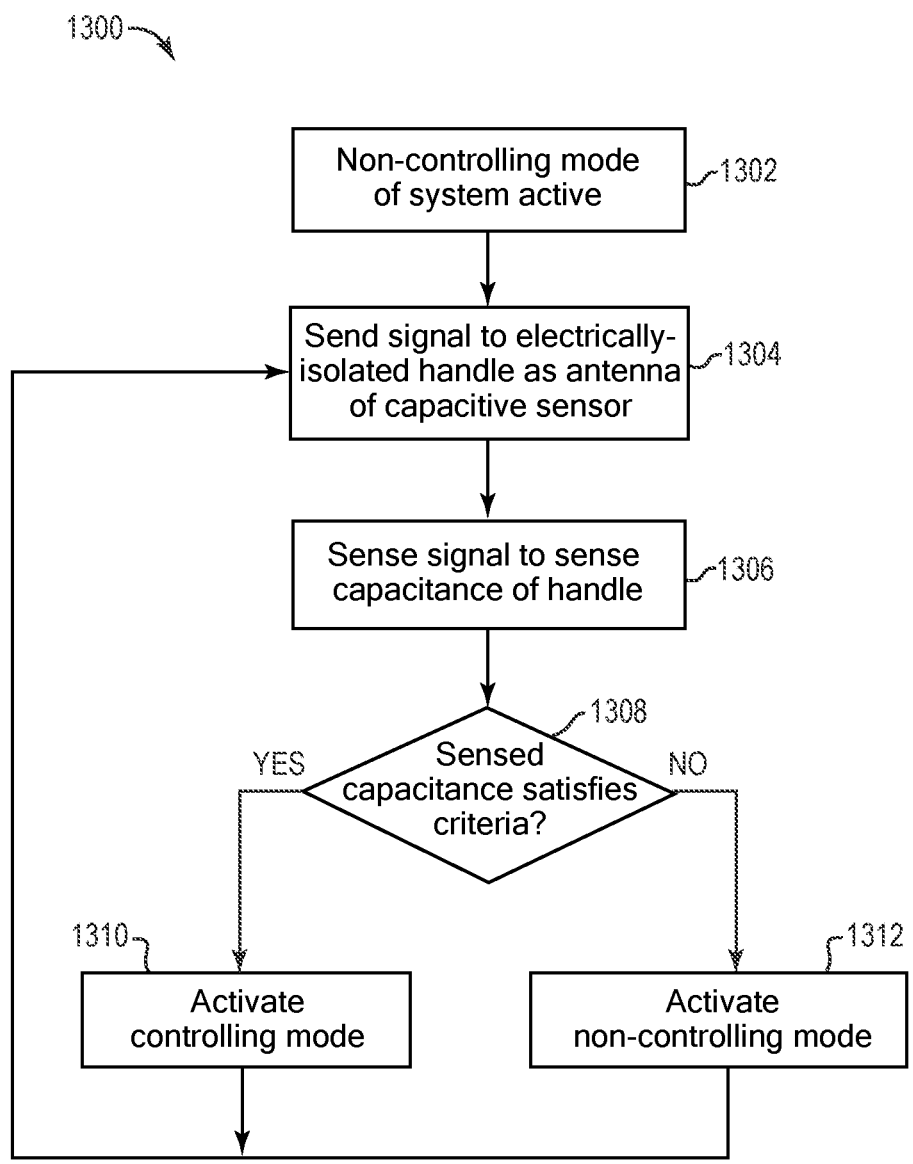
FIG. 13 is a flow diagram illustrating an example method to detect the presence of a user's hand operating a control input device, according to some implementations.

FIG. 13 is a flow diagram of an example method 1300 to detect, using a capacitive sensing system, the presence of a user's hand operating a control input device, according to some implementations. Method 1300 can, for example, be performed by a teleoperated system, e.g., teleoperated system 100 of FIG. 1 or other control system in which the control input device controls a manipulator device, e.g., one or more manipulator devices of manipulator system 104 of FIG. 1. Other systems including a control input device can also use method 1300. In some implementations, the control input device is a component of a user control system, e.g., user control system 102 of FIG. 1. The control input device can be or include, for example, a portion 300 or 400 of control input device 210 or 212, or another control input device as described herein. In some implementations, the method can be performed by a control unit coupled to the control input device. In some examples, the control unit can include one or more processors, e.g., microprocessors or other control circuits, some examples of which are described below with reference to FIG. 14.

A single control input device is referred to in method 1300 for explanatory purposes. Multiple control input devices can be similarly processed as described in method 1300, e.g., both control input devices 210 and 212 of FIG. 2. Some implementations can use a control input device having one or more features described herein with other types of systems, e.g., non-teleoperated systems, a virtual environment (e.g., medical simulation) having no physical manipulator device and/or no physical subject interacting with a physical manipulator device, etc.

In block 1302, a non-controlling mode of the teleoperated system (e.g., teleoperated system 100) is active. The non-controlling mode can also be considered a "safe mode" in which the control input devices are not enabled to provide control signals to a controlled device such as manipulator system 104. Thus, for example, the manipulator system is disconnected from the control input device in non-controlling mode. For example, the control input devices 210 and 212 can be manipulated by a user in non-controlling mode which will not cause corresponding controlled motion of a corresponding manipulator device of the manipulator system 104.

In block 1304, a signal is sent to an electrically-isolated handle of the control input device that operates as an antenna of a capacitive sensor. As described above, the handle, e.g., handle assembly including handle 402, can be electrically isolated from electrical ground using insulators on bearings, gears, and other components. A capacitive circuit can send a signal, e.g., an oscillating signal, onto the handle that acts as an antenna for the capacitive sensor.

In block 1306, the signal sent in block 1304 is sensed, e.g., by the capacitive sensor circuit that sent the signal or by a different sensor circuit. The signal indicates a current capacitance of the handle, e.g., based on a frequency or other characteristic of the signal, examples of which are described herein.

In block 1308, it is determined whether one or more detection criteria are satisfied based on the sensed capacitance. For example, the one or more detection criteria can include a threshold, and it can be determined whether the sensed capacitance of block 1306 satisfies the threshold. The threshold can be a threshold capacitance in some implementations or a threshold characteristic of the sensed signal or circuit (e.g., time constant, frequency, etc.). For example, a capacitance that is greater than a threshold capacitance (or characteristic that is greater than another threshold characteristic) can satisfy the threshold and indicate that an object is present within the sensing field of the capacitive sensor. Another example of satisfying a detection criterion can include matching a particular pattern in the sensed waveform that indicates sensed capacitance. In some examples, the sensed object can be a hand of a user contacting the handle or a nearby component of the control input device, or a hand that is located within a sensing distance of the handle. In some examples, the hand of the user can be contacting a grip portion of the handle 402 (e.g., one or more grip members 406) or central portion 407 of the handle 402 to cause the capacitance to change and satisfy the threshold as sensed by the sensor circuit.

If the one or more detection criteria are satisfied, then a detection of an object such as a hand of a user is considered to have occurred, and the method continues to block 1310. In block 1310, a controlling mode of the system is activated and/or enabled (and/or other states of the control input device and/or system are changed). The detection of the object is considered to indicate that a user is ready to start using the control input device, e.g., to control a manipulator device using the control input device, such that the controlling mode is activated and/or enabled. For example, in response to detecting the object, the capacitive sensor circuit (or other associated circuitry) generates one or more signals that can be sent to a control unit for the control input device. For example, in some implementations the signal can include a parameter, e.g., a value that indicates the detection of an object.

Controlling mode allows the manipulations of the control input device to control functions of a controlled manipulator device. For example, in a teleoperated system, the manipulations of the control input device can control corresponding motions, output functions (output of heat, electricity, etc.), and/or other functions of a corresponding manipulator device in controlling mode, such as moving an end effector in space, opening jaws of the end effector, outputting heat or other energy from the end effector, etc.

In some implementations, controlling mode is activated in response to a command from the user in addition to detecting user presence. In some implementations, user presence may also be required to be sensed by other presence sensing systems of the system in order to activate controlling mode. For example, a head presence sensor 214 as described for FIG. 2 can sense the head of a user in a location for operating the control input device. In some implementations, one or more devices of the control input device may be required to be moved by the user to particular positions, e.g., grip members 406 moved to a particular position matching a position and/or orientation of a controlled manipulator instrument. Thus, in some of these implementations, controlling mode is enabled in block 1310 but not activated unless user presence is otherwise detected. In some implementations, if such other presence sensing systems do not sense user presence, a negative result of block 1308 is determined.

In some implementations, the sensing system can detect whether the object is a hand or is a different type of object, e.g., based on a magnitude of sensed capacitance being within a particular capacitance range or based on a characteristic of the sensed signal. For example, a hand of a user may cause a different capacitance to be sensed than other types of objects. In some of these cases, if the object is not detected as a hand, a negative result of block 1308 is determined. In some implementations, any detected object within a sensing field of the capacitive sensor is considered to be a hand of a user.

In some implementations, one or more other system functions can be activated in block 1310 instead of or in addition to controlling mode. For example, one or more graphical user interfaces (GUIs) of the teleoperated system may be activated in block 1310 such that display objects or features of the GUIs are displayed. In some implementations, features or objects of the GUIs can be brightened in block 1310 from a prior dimmed state. In some implementations, power can be supplied to one or more components of the system, such as motors of the control input device to provide force feedback and/or gravity compensation, motors of a manipulator device to move arms and/or instruments, cameras for viewing an operating site, manipulator instrument functions (e.g., suction, irrigation, energy, etc.), etc. In some implementations, activated functions can include moving all or part of other components of a control system to starting positions via control of motors. Such components can include display devices (e.g., screens, viewers, etc.), foot pedals, seats, etc. The method returns to block 1304 to continue sensing for user presence.

If the one or more detection criteria are not satisfied in block 1308, then a detection of an object such as a hand of a user is not considered to have occurred, and the method continues to block 1312. In block 1312, the non-controlling mode of the system is activated (or maintained, if that mode is currently active). Lack of detection of an object is considered to indicate that the control input device is not being used, such that controlling mode is exited (if previously active) and the non-controlling mode is made active. For example, if controlling had been active, control of the manipulator device 104 is disconnected from the control input device based on the detection that the user is not operating the control input device. Furthermore, other states of the control input device and/or system can be changed. The method returns to block 1304 to continue sensing for user presence.

In some implementations, the system can enter additional or alternate states upon detecting that the controlling mode has been active and user presence is no longer detected (e.g., at block 1308). For example, upon loss of detection of the user's hand, a hold or pause of the controlling mode can be made active, such that, if the hand is again detected within a threshold period of time, the controlling mode can be re-entered more easily than when restarting the presence detection process from block 1302. For example, upon loss of detection of the user's hand, a power save mode of the system can be entered, and the power save mode can be exited when the hand is again detected.

In various implementations, a time delay can be used after a qualifying detection is made that causes the system to activate controlling mode and/or to activate non-controlling mode. For example, the time delay delays the activation of the controlling mode and/or non-controlling mode. In some examples, upon determining in block 1310 that controlling mode should be activated, the system can wait for a delay of 2 seconds or other time period before activating controlling mode. A similar delay can be provided after determining to activate non-controlling mode, such that the activation of the non-controlling mode is delayed. For example, in some implementations using a mechanically ungrounded control input device, the non-controlling mode is activated after a time period from determination of lack of user presence, e.g., to ensure that the user has not temporarily shifted the control input device in a hand.

In some implementations, multiple control input devices may be used, e.g., each control device being checked for user presence to allow controlling mode to be made active. In some examples, multiple control input devices 210 and 212 can be used as shown in FIG. 2. In some implementations, user presence must be detected at both control input devices to cause controlling mode to be made active for both control input devices. In some implementations, controlling mode can be made independently active for each control input device if user presence is detected at the respective control input device.

Various implementations can use different portions of the methods disclosed herein. The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods. In some implementations, some blocks can be removed, combined together, or supplemented with other blocks.

FIG. 14 is a block diagram of an example master-slave system 1400 which can be used with one or more features described herein. System 1400 includes a master device 1402 that a user may manipulate in order to control a slave device 1404 in communication with the master device 1402. In some implementations, master device 1402 can be, or can be included in, user control system 102 of FIG. 1. In some implementations, slave device 1404 can be, or can be included in, manipulator system 104 of FIG. 1. More generally, master device 1402 can be any type of device providing a control input device that can be physically manipulated by a user. Master device 1402 generates control signals C1 to Cx indicating positions, states, and/or changes of one or more control input devices in their degrees of freedom. Master device 1402 can also generate control signals (not shown) to control unit 1410 indicating selection of physical buttons and other manipulations by the user. The master device 1402 can also generate control signals to control unit 1410 including detection data associated with detection of user presence by a hand presence sensing system of the master device 1402 as described herein (e.g., indication of hand detection, detection parameters including distance, direction, and/or velocity of detected objects, etc.).

A control unit 1410 can be included in the master device 1402, in the slave device 1404, or in a separate device, e.g., an intermediary device between master device 1402 and slave device 1404. In some implementations, the control unit 1410 can be distributed among multiple of these devices. Control unit 1410 receives control signals C1 to Cx and generates actuation signals A1 to Ay, which are sent to slave device 1404. Control unit 1410 can also receive sensor signals B1 to By from the slave device 1404 that indicate positions, orientations, states, and/or changes of various slave components (e.g., manipulator arm elements). Control unit 1410 can include general components such as a processor 1412, memory 1414, and interface hardware 1416 and 1418 for communication with master device 1402 and slave device 1404, respectively. Processor 1412 can execute program code and control basic operations of the system 1400, including functions related to sensing the switch mechanisms described herein, and can include one or more processors of various types, including microprocessors, application specific integrated circuits (ASICs), and other electronic circuits. Memory 1414 can store instructions for execution by the processor and can include any suitable processor-readable storage medium, e.g., random access memory (RAM), read-only memory (ROM), electrical erasable read-only memory (EEPROM), flash memory, etc. Various other input and output devices can also be coupled to the control unit 1410, e.g., display(s) 1420 such as the viewer 213 of the user control system 102 and/or display 124 of FIGS. 1 and 2. Presence sensors 1422 can provide signals to control unit 1410 indicating detection of user presence and/or parameters related to such detection; for example, presence sensors 1422 can be the capacitive sensing systems described herein that provide sensor signals to control unit 1410. In some implementations, sensors 1422 can include head presence sensor 214 of FIG. 2.

In this example, control unit 1410 includes a mode control module 1440, a controlling mode module 1450, and a non-controlling mode module 1460. Other implementations can use other modules, e.g., a force output control module, sensor input signal module, etc. In some implementations, the modules 1440, 1450, and 1460 can be implemented using the processor 1412 and memory 1414, e.g., program instructions stored in memory 1414 and/or other memory or storage devices connected to control unit 1410.

Mode control module 1440 can detect when a user initiates a controlling mode and a non-controlling mode of the system, e.g., by user selection of controls, sensing a presence of a user at a user control system or control input device, sensing required manipulation of a control input device, etc. The mode control module can set the controlling mode or a non-controlling mode of the control unit 1410 based on one or more control signals C1 to Cx.

In some implementations, controlling mode module 1450 may be used to control a controlling mode of control unit 1410. Controlling mode module 1450 can receive control signals C1 to Cx and can generate actuation signals A1 to Ay that control actuators of the slave device 1404 and cause it to follow the movement of master device 1402, e.g., so that the movements of slave device 1404 correspond to a mapping of the movements of master device 1402. Controlling mode module 1450 can also be used to control forces on the control input device of the master device 1402, e.g., forces output on one or more components of the control input device, e.g., grip members, using one or more control signals D1 to Dx output to actuator(s) used to apply forces to the components, e.g., to the grip members of the control input device, in a rotational degree of freedom of the control input device, on arm links coupled to the control input device, etc. In some examples, control signals D1 to Dx can be used to provide force feedback, gravity compensation, etc.

In some implementations, a non-controlling mode module 1460 may be used to control a non-controlling mode of system 1400. In the non-controlling mode, movement in one or more degrees of freedom of master device 1402, or other manipulations of master device 1402, has no effect on the movement of one or more components of slave 1404. In some implementations, non-controlling mode can include one or more other operating modes of the control unit 1410, e.g., a selection mode in which movement of the control input device in one or more of its degrees of freedom and/or selection of the control switches of the control input device can control selection of displayed options, e.g., in a graphical user interface displayed by display 1420 and/or other display device. A viewing mode can allow movement of the control input device to control a display provided from cameras, or movement of cameras, that may not be included in the slave device 1404. Control signals C1 to Cx can be used by the non-controlling mode module 1460 to control such elements (e.g., cursor, views, etc.) and control signals D1 to Dx can be determined by the non-controlling mode module to cause output of forces on the control input device during such non-controlling modes, e.g., to indicate to the user interactions or events occurring during such modes.

Some implementations described herein, e.g., method 1300, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a RAM, a ROM, flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g., field-programmable gate array (FPGA), complex programmable logic device), general purpose processors, graphics processors, ASICs, and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A control input device comprising:
a support structure coupled to electrical ground;
a handle moveable in one or more degrees of freedom with reference to the support structure, the handle including a rotatable grip member;
one or more electrical isolation elements coupled between the handle and the support structure; and
a capacitive sensor circuit electrically coupled to the handle;
wherein the grip member of the handle is an antenna for the capacitive sensor circuit; and
wherein the grip member is electrically isolated from the electrical ground by the one or more electrical isolation elements.

2. The control input device of claim 1,
wherein the one or more electrical isolation elements include an electrical isolation element having at least two portions, wherein a first portion of the at least two portions includes an insulative material and a second portion of the at least two portions includes a conductive material.

3. The control input device of claim 1, wherein:
at least one of the one or more electrical isolation elements includes a bearing, wherein the bearing includes a first bearing portion coupled to the support structure and a second bearing portion coupled to the handle.

4. The control input device of claim 3, wherein:
the first bearing portion includes a first electrically insulative layer that contacts the support structure; or
the second bearing portion includes a second electrically insulative layer that contacts the handle.

5. The control input device of claim 3, wherein:
the bearing includes a first element, a second element, and a plurality of balls each made of an electrically insulative material;
the first element is coupled to the support structure;
the second element is coupled to the handle; and
the plurality of balls is positioned between the first element and the second element.

6. The control input device of claim 3, wherein:
the handle comprises a proximal end and a distal end, and a roll axis is defined through the proximal and distal ends; and
the bearing supports a roll degree of freedom of the handle about the roll axis with reference to the support structure.

7. The control input device of claim 3, wherein:
the control input device further includes a cylindrical member rotatable about a roll axis of the handle;
the cylindrical member provides a roll degree of freedom to the handle; and
the cylindrical member is coupled to the bearing.

8. The control input device of claim 1, wherein:
at least one of the one or more electrical isolation elements includes a drive mechanism configured to transmit force from an actuator to the handle.

9. The control input device of claim 8, wherein:
the drive mechanism includes a gear mechanism;
the gear mechanism includes a first gear and a second gear;
the first gear is coupled to the handle and engages the second gear;
the second gear is coupled to the support structure; and
at least one of the first gear or the second gear includes an insulator that electrically isolates the handle from the electrical ground via the gear mechanism.

10. The control input device of claim 9, wherein:
the first and second gears each include gear teeth; and
the insulator includes at least one of:
an electrically insulative layer on the gear teeth of the first gear, the second gear, or both the first and second gears;
an anodized surface on the gear teeth of the first gear, the second gear, or both the first and second gears;
an electrically insulative portion of the first gear coupled to an electrically conductive portion of the first gear; or
an electrically insulative portion of the second gear coupled to an electrically conductive portion of the second gear.

11. The control input device of claim 9, wherein:
the first gear includes an aperture and a surface within the aperture;
the control input device further includes a rotatable cylindrical member that extends through the aperture in the first gear and couples the gear mechanism to the handle; and
the insulator includes at least one of:
an insulative layer or a sleeve on at least a portion of the cylindrical member, or
an insulative layer on the surface of the first gear within the aperture.

12. The control input device of claim 1, wherein:
the capacitive sensor circuit is configured to detect a capacitance of the handle with reference to the electrical ground based on an electrical signal applied from the capacitive sensor circuit to the handle.

13. The control input device of claim 1, wherein:
the handle is rotatable in one or more rotational degrees of freedom about corresponding one or more rotational axes of the handle with reference to the support structure;
the handle includes a central portion;
the grip member is rotatably coupled to the central portion;
the grip member is coupled to the central portion by a coupling;
wherein the coupling provides electrical conductivity between the grip member and the central portion of the handle.

14. The control input device of claim 1, wherein:
the control input device further includes a finger loop coupled to the handle; and
the finger loop includes conductive metallic elements and is electrically conductive.

15. The control input device of claim 1, wherein:
the control input device further includes an element coupled to the grip member; and
the element is configured to cause the grip member to move by translating along a linear axis of the handle with reference to the support structure;
the control input device further includes a cylindrical member and a rotary electrical connector;
the cylindrical member is rotatable about a central axis of the handle and provides a roll degree of freedom to the handle; and
the rotary electrical connector is coupled between the capacitive sensor circuit and the cylindrical member.

16. The control input device of claim 1, wherein:
the control input device is mechanically grounded.

17. The control input device of claim 1, wherein:
the control input device is mechanically ungrounded.

18. The control input device of claim 1, wherein:
the control input device further includes one or more control input sensors;
the one or more control input sensors sense one or more positions, one or more orientations, or one or more positions and orientations of the handle in the one or more degrees of freedom;
the control input device is included in a teleoperated surgical system;
the support structure is coupled to a gimbal mechanism that provides multiple degrees of freedom to the support structure and to the handle;
the teleoperated surgical system includes a controlling mode in which movement of the handle in the one or more degrees of freedom activates one or more functions of a manipulator device of the teleoperated surgical system; and
a capacitance sensed by the capacitive sensor circuit and that indicates presence of a hand of a user at the control input device enables activation of the controlling mode of the teleoperated surgical system.

19. A method comprising:
sending an electrical signal from a capacitive sensor circuit to a handle of a control input device, the handle being isolated from an electrical ground via one or more isolation elements, wherein at least one of the one or more isolation elements includes at least one of a bearing including a first insulator, or a drive mechanism including a second insulator;
sensing, by the capacitive sensor circuit, a first capacitance of the handle based on the electrical signal; and
determining that a user presence has been sensed at the control input device in response to the sensed first capacitance of the handle satisfying one or more detection criteria.

20. The method of claim 19, wherein:
the handle is an antenna for the capacitive sensor circuit; and
the user presence includes user contact received at a grip portion of the handle; and
the method further includes sensing, by the capacitive sensor circuit, a second capacitance of the handle based on the electrical signal; and
the method further includes determining that the user presence has been removed from the control input device in response to the second capacitance of the handle not satisfying the one or more detection criteria.

21. A control input device comprising:
a support structure;
a handle moveable in one or more degrees of freedom with reference to the support structure;
an electrical isolation element coupled between the handle and the support structure, wherein the handle is electrically isolated from the electrical ground through the electrical isolation element, wherein the electrical isolation element includes a bearing, and
   wherein the bearing includes a first bearing portion coupled to the support structure and a second bearing portion coupled to the handle;
a capacitive sensor circuit electrically coupled to the handle;
wherein the handle is an antenna for the capacitive sensor circuit; and
wherein the handle is electrically isolated from the electrical ground.

22. A control input device comprising:
a support structure;
a handle moveable in one or more degrees of freedom with reference to the support structure;
an electrical isolation element coupled between the handle and the support structure, wherein the handle is electrically isolated from the electrical ground through the electrical isolation element, wherein the electrical isolation element includes a drive mechanism configured to transmit force from an actuator to the handle;
a capacitive sensor circuit electrically coupled to the handle;
wherein the handle is an antenna for the capacitive sensor circuit; and
wherein the handle is electrically isolated from the electrical ground.

23. A control input device comprising:
a support structure;
a handle moveable in one or more degrees of freedom with reference to the support structure; and
a capacitive sensor circuit electrically coupled to the handle;
wherein:
   the handle is an antenna for the capacitive sensor circuit,
   the handle is electrically isolated from the electrical ground,
   the handle is rotatable in one or more rotational degrees of freedom about one or more corresponding rotational axes of the handle with reference to the support structure,
   the handle includes a grip member and a central portion,
   the grip member is rotatably coupled to the central portion by a coupling,
   the coupling includes an insulator that provides electrical isolation of the handle from the electrical ground.

24. The control input device of claim 23, wherein the insulator includes an anodized surface on the coupling.

25. A control input device comprising:
a support structure;
a handle moveable in one or more degrees of freedom with reference to the support structure; and
a capacitive sensor circuit electrically coupled to the handle;
wherein:
   the handle includes a grip member;
   the control input device further includes an element coupled to the grip member; and
   the element is configured to cause the grip member to move by translating along a linear axis of the handle with reference to the support structure;
   the control input device further includes a cylindrical member and a rotary electrical connector;
   the cylindrical member is rotatable about a central axis of the handle and provides a roll degree of freedom to the handle; and
   the rotary electrical connector is coupled between the capacitive sensor circuit and the cylindrical member.

* * * * *